(12) United States Patent
Henkel

(10) Patent No.: US 8,141,330 B2
(45) Date of Patent: Mar. 27, 2012

(54) SYSTEMS AND METHODS OF AUTOMATED TABLET DISPENSING, PRESCRIPTION FILLING, AND PACKAGING

(75) Inventor: Claus Henkel, Cartersville, GA (US)

(73) Assignee: KNAPP Logistics Automation, Inc., Kennesaw, GA (US)

( * ) Notice: Subject to any disclaimer, the term of this patent is extended or adjusted under 35 U.S.C. 154(b) by 1596 days.

(21) Appl. No.: 11/134,113

(22) Filed: May 20, 2005

(65) Prior Publication Data

US 2006/0025884 A1    Feb. 2, 2006

Related U.S. Application Data

(60) Provisional application No. 60/572,955, filed on May 20, 2004.

(51) Int. Cl.
*B65B 57/10* (2006.01)
(52) U.S. Cl. ............................................. 53/500; 53/237
(58) Field of Classification Search .................... 53/500, 53/237, 247, 473
See application file for complete search history.

(56) References Cited

U.S. PATENT DOCUMENTS

| | | | |
|---|---|---|---|
| 2,530,230 A | 11/1950 | Cozzoli |
| 2,665,775 A | 1/1954 | Smith |
| 2,689,677 A | 9/1954 | Unger |
| 2,708,996 A | 5/1955 | Skillman |
| 2,742,184 A | 4/1956 | Yerkes et al. |
| 2,838,893 A | 6/1958 | Sickel |
| 2,865,532 A | 12/1958 | Smith |
| 2,896,381 A | 7/1959 | Lange |
| 3,023,851 A | 3/1962 | Stiller |
| 3,047,347 A | 7/1962 | Groves |
| 3,144,958 A | 8/1964 | Gumpertz |
| 3,160,793 A | 12/1964 | Colburn et al. |
| 3,179,288 A | 4/1965 | Davy |
| 3,185,851 A | 5/1965 | D'Emilio |
| 3,194,433 A | 7/1965 | Heselov |
| 3,196,276 A | 7/1965 | Naab |
| 3,206,062 A | 9/1965 | Rappaport |
| 3,227,325 A | 1/1966 | Bates |
| 3,242,881 A | 3/1966 | Schafer |
| 3,245,194 A | 4/1966 | Carski |
| 3,310,199 A | 3/1967 | Roberts et al. |
| 3,312,372 A | 4/1967 | Cooper, Jr. |

(Continued)

FOREIGN PATENT DOCUMENTS

CA    936501    11/1973

(Continued)

OTHER PUBLICATIONS

Automated Order Selection Systems, SI Handling Systems, Inc.

(Continued)

*Primary Examiner* — Sameh H. Tawfik
(74) *Attorney, Agent, or Firm* — Kilpatrick, Townsend & Stockton LLP

(57) ABSTRACT

Systems and methods of automatically dispensing tablets are disclosed. The systems and methods of the invention provide a highly secure, highly accurate and rapid means of dispensing tablets. The system includes an automatic dispensing tablet dispensing system as shown in the Figures and provides a means of lowering errors while preventing unauthorized tampering by non-authorized personnel. Moreover, the invention relates to systems and methods for packaging vials, packaging items from totes, and packaging items from totes with vials.

20 Claims, 28 Drawing Sheets

U.S. PATENT DOCUMENTS

| | | |
|---|---|---|
| 3,381,856 A | 5/1968 | Hrdina |
| 3,383,011 A | 5/1968 | Reed et al. |
| 3,394,798 A | 7/1968 | Sako |
| 3,397,642 A | 8/1968 | Petrucci et al. |
| 3,410,450 A | 11/1968 | Fortenberry |
| 3,417,542 A | 12/1968 | Merrill et al. |
| 3,436,736 A | 4/1969 | Platt et al. |
| 3,437,051 A | 4/1969 | Hrdina |
| 3,556,342 A | 1/1971 | Guarr |
| 3,584,226 A | 6/1971 | Lerner |
| 3,599,152 A | 8/1971 | Williams |
| 3,606,959 A | 9/1971 | Stonor |
| 3,653,176 A | 4/1972 | Gess |
| 3,662,517 A | 5/1972 | Tascher et al. |
| 3,677,437 A | 7/1972 | Haigler |
| 3,698,450 A | 10/1972 | Taylor et al. |
| 3,722,740 A | 3/1973 | List |
| 3,730,388 A | 5/1973 | Bender |
| 3,732,544 A | 5/1973 | Obland |
| 3,746,130 A | 7/1973 | Bullas |
| 3,746,211 A | 7/1973 | Burgess, Jr. |
| 3,753,158 A | 8/1973 | Prescott |
| 3,771,693 A | 11/1973 | Jessick |
| 3,780,907 A | 12/1973 | Colburn et al. |
| 3,809,296 A | 5/1974 | Croslin |
| 3,837,139 A | 9/1974 | Roseberg |
| 3,852,941 A | 12/1974 | Bross |
| 3,871,156 A | 3/1975 | Koenig et al. |
| 3,878,967 A | 4/1975 | Joslin et al. |
| 3,885,702 A | 5/1975 | Joslin et al. |
| 3,907,100 A | 9/1975 | Ranford et al. |
| 3,915,292 A | 10/1975 | Brown |
| 3,917,045 A | 11/1975 | Williams et al. |
| 3,939,626 A | 2/1976 | Cioni et al. |
| 3,940,909 A | 3/1976 | Cioni et al. |
| 3,950,918 A | 4/1976 | Morrow et al. |
| 3,985,264 A | 10/1976 | Shaw et al. |
| 3,998,356 A | 12/1976 | Christensen |
| 4,013,192 A | 3/1977 | Pillon |
| 4,085,782 A | 4/1978 | Carlson |
| 4,091,932 A | 5/1978 | Bigarella |
| 4,118,914 A | 10/1978 | Shields |
| 4,150,766 A | 4/1979 | Westendorf et al. |
| 4,199,013 A | 4/1980 | Reich et al. |
| 4,267,942 A | 5/1981 | Wick, Jr. et al. |
| 4,293,845 A | 10/1981 | Villa-Real |
| 4,350,243 A | 9/1982 | Weyandt |
| 4,360,125 A | 11/1982 | Martindale et al. |
| 4,362,455 A | 12/1982 | Hirose |
| 4,382,527 A | 5/1983 | Lerner |
| 4,434,602 A | 3/1984 | Culpepper |
| 4,449,640 A | 5/1984 | Finkelstein |
| 4,473,884 A | 9/1984 | Behl |
| 4,501,339 A * | 2/1985 | Fukuda ...................... 177/25.14 |
| 4,542,808 A | 9/1985 | Lloyd, Jr. et al. |
| 4,546,901 A | 10/1985 | Buttarazzi |
| 4,567,988 A | 2/1986 | Weibel |
| 4,573,606 A | 3/1986 | Lewis et al. |
| 4,586,622 A | 5/1986 | Walldorf |
| 4,632,631 A | 12/1986 | Dunlap |
| 4,655,026 A | 4/1987 | Wigoda |
| 4,664,289 A | 5/1987 | Shimizu et al. |
| 4,668,219 A | 5/1987 | Isreal |
| 4,672,553 A | 6/1987 | Goldberg |
| 4,674,259 A * | 6/1987 | Hills ................................ 53/202 |
| 4,674,651 A | 6/1987 | Scidmore et al. |
| 4,674,652 A | 6/1987 | Aten et al. |
| 4,686,815 A | 8/1987 | Zils et al. |
| 4,693,057 A | 9/1987 | Rittinger et al. |
| 4,695,954 A | 9/1987 | Rose et al. |
| 4,725,997 A | 2/1988 | Urquhart et al. |
| 4,733,362 A | 3/1988 | Haraguchi |
| 4,766,542 A | 8/1988 | Pilarczyk |
| 4,767,023 A | 8/1988 | Hackmann et al. |
| 4,790,118 A | 12/1988 | Chilcoate |
| 4,804,093 A | 2/1989 | Durow |
| 4,805,377 A | 2/1989 | Carter |
| 4,823,623 A | 4/1989 | Carpenter et al. |
| 4,834,264 A | 5/1989 | Siegel et al. |
| 4,842,028 A | 6/1989 | Kaufman et al. |
| 4,847,764 A | 7/1989 | Halvorson |
| 4,850,104 A | 7/1989 | Matrone et al. |
| 4,853,546 A | 8/1989 | Abe et al. |
| 4,867,315 A | 9/1989 | Baldwin |
| 4,869,392 A | 9/1989 | Moulding, Jr. et al. |
| 4,870,799 A | 10/1989 | Bergerioux et al. |
| 4,901,841 A | 2/1990 | Haggerty et al. |
| 4,903,861 A | 2/1990 | Yuyama |
| 4,918,604 A | 4/1990 | Baum |
| 4,971,513 A | 11/1990 | Bergerioux et al. |
| 4,972,657 A | 11/1990 | McKee |
| 4,980,292 A | 12/1990 | Elbert et al. |
| 4,984,709 A | 1/1991 | Weinstein |
| 4,999,977 A * | 3/1991 | Briscoe et al. .................. 53/501 |
| 5,005,340 A * | 4/1991 | Mojden ......................... 53/500 |
| 5,014,875 A | 5/1991 | McLaughlin et al. |
| 5,018,644 A | 5/1991 | Hackmann et al. |
| 5,027,938 A | 7/1991 | Haggarty et al. |
| 5,047,948 A | 9/1991 | Turner |
| 5,097,652 A | 3/1992 | Inamura et al. |
| 5,108,005 A | 4/1992 | Mosbacher |
| 5,208,762 A | 5/1993 | Charhut et al. |
| 5,337,919 A | 8/1994 | Spaulding et al. |
| 5,348,061 A | 9/1994 | Riley et al. |
| 5,377,864 A | 1/1995 | Blechl et al. |
| 5,431,299 A | 7/1995 | Brewer et al. |
| 5,481,855 A * | 1/1996 | Yuyama ......................... 53/493 |
| 5,499,483 A * | 3/1996 | Oikawa ............................ 53/53 |
| 5,502,944 A | 4/1996 | Kraft et al. |
| 5,638,657 A | 6/1997 | Archer et al. |
| 5,660,305 A | 8/1997 | Lasher et al. |
| 5,709,063 A * | 1/1998 | Yuyama et al. .................. 53/154 |
| 5,713,487 A | 2/1998 | Coughlin |
| 5,720,154 A | 2/1998 | Lasher et al. |
| RE35,743 E | 3/1998 | Pearson |
| 5,752,368 A | 5/1998 | Tobe |
| 5,765,606 A | 6/1998 | Takemasa et al. |
| 5,771,657 A | 6/1998 | Lasher et al. |
| 5,812,410 A | 9/1998 | Lion et al. |
| 5,838,575 A | 11/1998 | Lion |
| 5,839,257 A | 11/1998 | Soderstrom et al. |
| 5,852,911 A | 12/1998 | Yuyama et al. |
| 5,907,493 A | 5/1999 | Boyer et al. |
| 6,036,812 A | 3/2000 | Williams et al. |
| 6,170,230 B1 | 1/2001 | Chudy et al. |
| 6,208,911 B1 | 3/2001 | Yamaoka et al. |
| 6,256,967 B1 | 7/2001 | Hebron et al. |
| 4,847,764 C1 | 9/2001 | Halvorson |
| 6,317,648 B1 | 11/2001 | Sleep et al. |
| RE37,471 E | 12/2001 | Jagger |
| 6,363,687 B1 | 4/2002 | Luciano et al. |
| 6,370,841 B1 | 4/2002 | Chudy et al. |
| 6,385,943 B2 | 5/2002 | Yuyama et al. |
| 6,421,584 B1 * | 7/2002 | Norberg et al. ................ 700/242 |
| RE37,829 E | 9/2002 | Charhut et al. |
| 6,449,927 B2 | 9/2002 | Hebron et al. |
| 6,504,387 B1 | 1/2003 | Shail et al. |
| 6,522,945 B2 | 2/2003 | Sleep et al. |
| 6,625,952 B1 | 9/2003 | Chudy et al. |
| 6,681,149 B2 | 1/2004 | William et al. |
| 6,681,550 B1 | 1/2004 | Aylward |
| 6,684,914 B2 | 2/2004 | Gershman et al. |
| 6,742,671 B2 | 6/2004 | Hebron et al. |
| 2004/0088187 A1 | 5/2004 | Chudy et al. |

FOREIGN PATENT DOCUMENTS

| | | |
|---|---|---|
| CA | 1 317 262 | 5/1993 |
| FR | 2 670 179 | 6/1992 |
| GB | 1 168 758 | 10/1969 |
| GB | 1 411 951 | 10/1975 |
| GB | 1 484 893 | 9/1977 |
| JP | 51-000792 | 1/1976 |
| JP | 52-47400 | 12/1977 |

| | | |
|---|---|---|
| JP | 61-104904 | 5/1986 |
| JP | 63-208410 | 8/1988 |
| JP | 1-288265 | 11/1989 |
| JP | 2-028417 | 1/1990 |
| WO | WO 86/06048 | 10/1986 |
| WO | WO 94/12393 | 6/1994 |

OTHER PUBLICATIONS

Use of Automatic Dispensing Machines Spreads in Industry, Drug Topics—The News Magazine for Today's Pharmacies, Apr. 7, 1986.

* cited by examiner

Legend:
① Empty Vials
② Empty Vials Waiting to be Filled
③ Full Vials
④ Partially Filled Vials
← Direction of Conveyor Motion ized tablet dispensing that provide high security, controlled and reduced replenishment, efficiency, and ease of use.
SYSTEMS AND METHODS OF AUTOMATED TABLET DISPENSING, PRESCRIPTION FILLING, AND PACKAGING This invention claims priority under 35 USC §119 to U.S. Provisional Application No. 60/572,955 filed on May 20, 2004, the contents of which are hereby incorporated by reference in its entirety.

FIELD OF THE INVENTION

This invention relates to systems and methods of automated tablet dispensing that provide high security and controlled replenishment. The invention also relates to prescription filling systems including a plurality of automated tablet dispensers and packaging capabilities.

BACKGROUND OF THE INVENTION

Existing tablet counting and dispensing systems generally employ serial processes in which bulk drug is emptied into a device that counts the tablets directly into empty bottles or vials. Such devices generally include numerous, up to several hundred, containers for holding numerous types of drugs. Once the counter has emptied out all of the tablets of a container for a particular drug, a technician refills the container from bulk storage containers before the device begins counting again. As bulk drug is emptied into the counting device, spillage often occurs. Many existing tablet counting and dispensing systems, such as Baker cells, typically include rotating bowls that tend to grind on tablets causing excess dust. After some time, the resulting dust is sufficient to cause errors in counting to occur. Additionally, the system may need to be cleaned as many as four or more times per day in order to maintain the system and improve accuracy. Generally, if the system is not cleaned, one also has problems with cross-contamination. Furthermore, existing systems fail to provide a level of security that is as high as desired by most in the industry given the sensitive nature of pharmaceuticals and the possibility of tampering with tablets or capsules that end up on the shelf of the local drug store and/or into the hands of patients and/or households. Accordingly, there is a need for methods and systems of automated tablet dispensing that provide high security, controlled and reduced replenishment, efficiency, and ease of use.

DETAILED DESCRIPTION OF THE INVENTION

Figure 1:
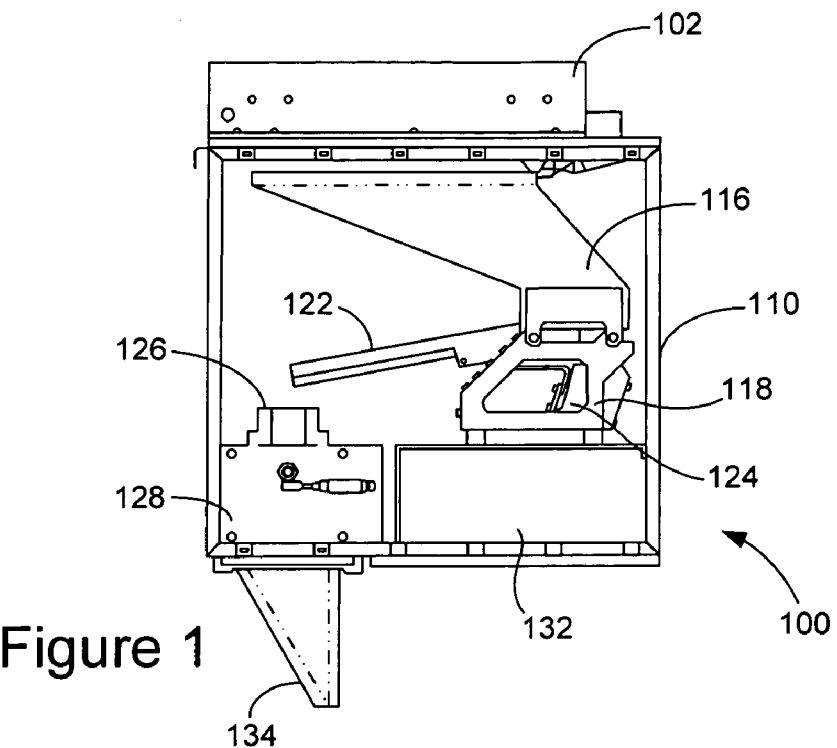
FIG. 1 shows a side view of an embodiment of a system for automated tablet dispensing according to the present invention.
Figure 25:
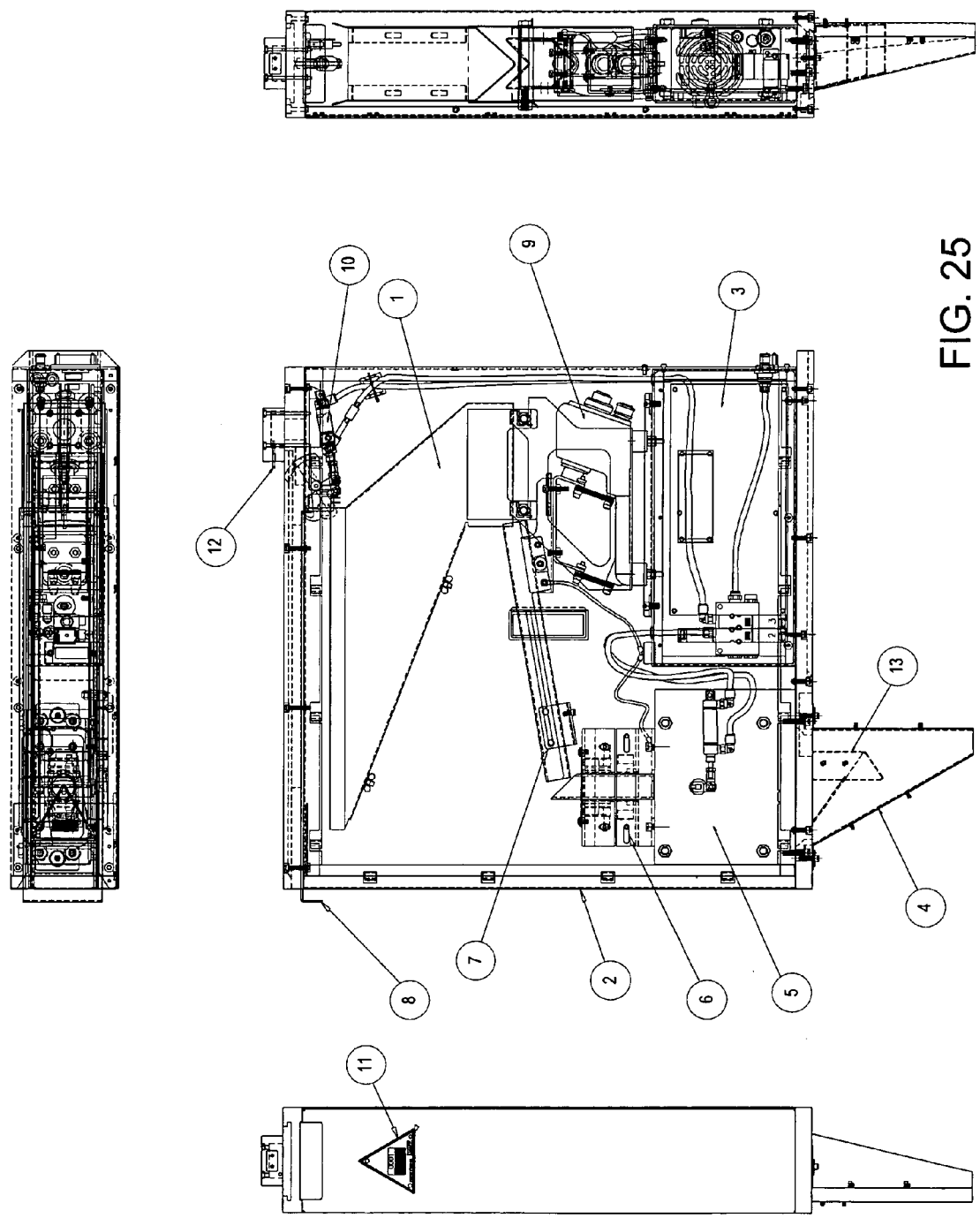
FIG. 25 shows several views of an embodiment of an automated tablet dispensing system according to this invention.

The present invention provides an automated tablet counting and dispensing system that provides patient safety, high operating reliability, and ease of use for authorized personnel. An exemplary embodiment of an automated tablet dispensing system 100 includes a canister 102, a nozzle assembly 134, and a counter 109 that includes a hopper assembly 114 with a dispenser reserve 116, vibrating feeder 124, and one or more singulation channels 122; a scanner or sensor 126; a buffer assembly 128; and a control board enclosure 132, as shown in FIG. 1. Several views of an embodiment of an automated tablet dispensing system according to this invention are also shown in FIG. 25. Canister 102 is removed from counter 109 and filled with bulk drug product in a secure room, which is a location with restricted access. Once canister 102 is filled, it is returned to the room in which its matching counter is located. Canister 102 is docked with counter 109, and the drug product empties completely into counter 109 from canister 102. Once the drug product is emptied into counter 109, canister 102 may be removed and refilled in the secure room while counter 109 performs the operations of counting the drug product into vials, bottles, or similar containers. The canister can be designed in a way that allows for replenishment of the canister during the counting of the tablets process. In other words, the system does not need to be turned off when a canister is being replenished during counting. In an exemplary embodiment, the canister is designed so that no one has physical access during the replenishment of the canister. The counter door is generally closed and locked so that there is no access to the counter or to the canister by unauthorized personnel. Moreover, in one embodiment, when the canister is in place on the counter, there is a locking mechanism that prevents either of the counter or canister from being accessed by unauthorized personnel.

It should be apparent to those of ordinary skill in the art that one of the purposes of the canister is to transport product from bulk containers to the ATD system (automated tablet dispensing system). In one embodiment, an access door, and preferably a sliding access door may be present at the bottom of the canister. The door can be pulled out to enable access to the canister chamber where the product will be stored. After closing the door, a tamper proof security tag can be placed through openings on either side of the canister so as to preclude access by unauthorized personnel. Those of skill in the art will recognize that a security tag can be added in other areas of the canister so as to prevent access by unauthorized personnel. In one embodiment, the canister can be provided with a triangular label with a 2D barcode and a four digit number or alternatively, an RF chip electronic verification system. The barcode and number can be used to verify the correct location of the canister before, during, or after dispensing tablets. Moreover, the canister may have an electronic number stored in a chip at the back. The electronic number can be read through two spring loaded pins that make contact at the back of the canister, when the canister is in use.

The use of multiple automated tablet dispensing systems 100 operating in parallel in a prescription filling system provides increased efficiency, in contrast to the serial processing utilized in existing prescription filling lines. An exemplary embodiment of a prescription filling system according to this invention is described in additional detail below beginning with reference to FIG. 22.

Figure 2:
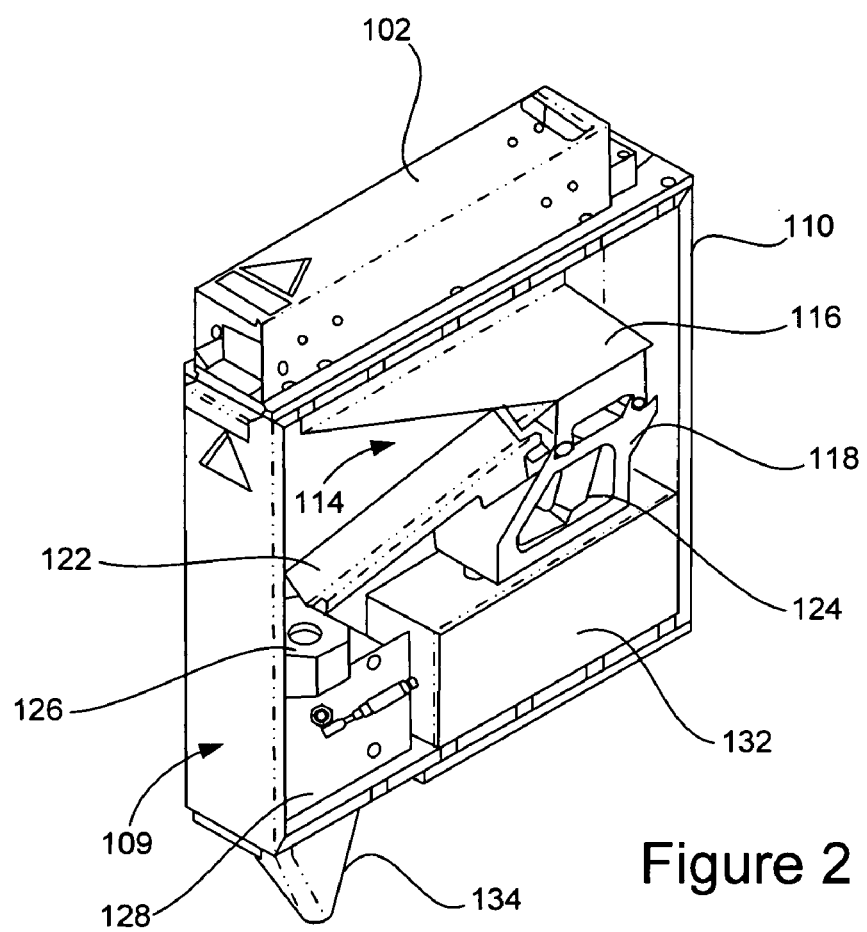
FIG. 2 shows a perspective view of the automated tablet dispensing system of FIG. 1.

As shown in FIGS. 1 and 2, an exemplary embodiment of a tablet dispensing system 100 according to this invention includes canister 102, counter 109 that includes hopper assembly 114 with dispenser reserve 116, vibrating feeder 124, and singulation channel 122; sensor 126; buffer assembly 128; and control board 132; and nozzle assembly 134 extending from counter 109. In one embodiment, each canister is dedicated to a counter with a unique serial number such that a canister can only be used to refill its assigned counter. Because of these dedicated canisters and counters, the possibility of cross-contamination of multiple counters is eliminated. In one embodiment, a tablet dispensing system may fill one or more different sizes of vials with tablets and according to prescription orders, while maintaining controlled replenishment and ensuring patient safety.

Figure 24:
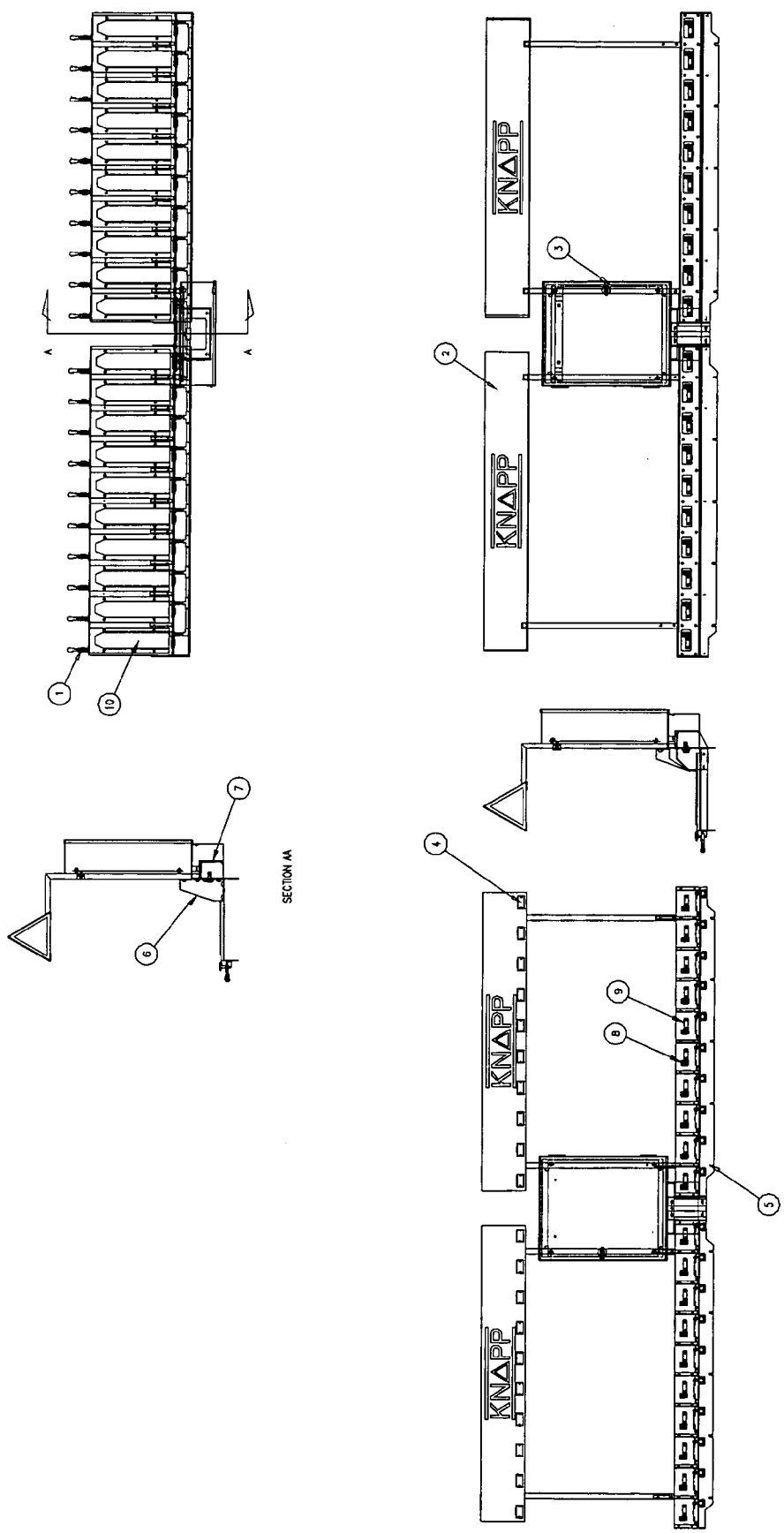
FIG. 24 shows several views of an embodiment of a sub-frame assembly for placement of multiple automated tablet dispensing systems according to this invention.

A shelf docking station, such as the exemplary sub-frame assembly shown in FIG. 24, utilizes a plastic plate, to securely position the counter, which enables connections to electrical power and computer equipment. A base plate of the counter securely attaches the counter to the shelf docking station. In an exemplary embodiment of a prescription filling system, shelf structure may be equipped with numerous docking stations, 50, 100, 460, or any other number (for example the sub-frame assembly shown in FIG. 24 includes 20 spaces for docking counters and multiple sub-frame assemblies may be used), to hold numerous automated tablet dispensing systems (this is further described below beginning with reference to FIG. 22). A permanent barcode serial number tag (not shown), which is a unique barcode, is displayed on each shelf docking station. A permanent visual number tag (not shown), which is a visually readable number on each shelf docking station, is also displayed. A security identification chip, embedded within each station, provides a unique electronic signature to the central computer system. The ID chip cannot be altered or reprogrammed enabling a very secure barcode validation by the central computer. A refill docking station (not shown), located in a secure room and used for refilling canisters, includes a hopper for bulk product, a canister hold station, a barcode scanner, and a computer terminal. A refill docking station may receive different canisters for emptying drug product from bulk containers into the canister in a tightly controlled manner. Because canisters are filled separately from counters, there is reduced spillage of drug product in and around the counters. Usually the filling of canisters takes place in a secure room where there is no access to the canisters by unauthorized personnel.

Figure 3:
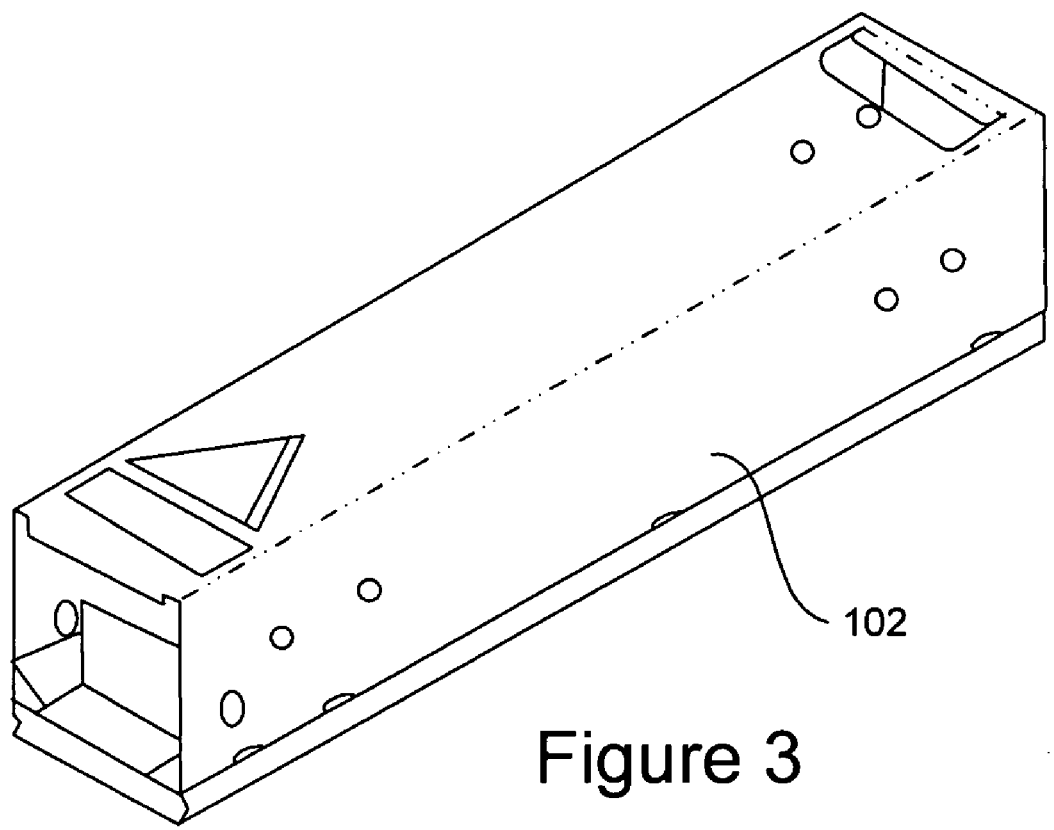
FIG. 3 shows a perspective view of a canister of the automated tablet dispensing system of FIG. 1.
Figure 4:
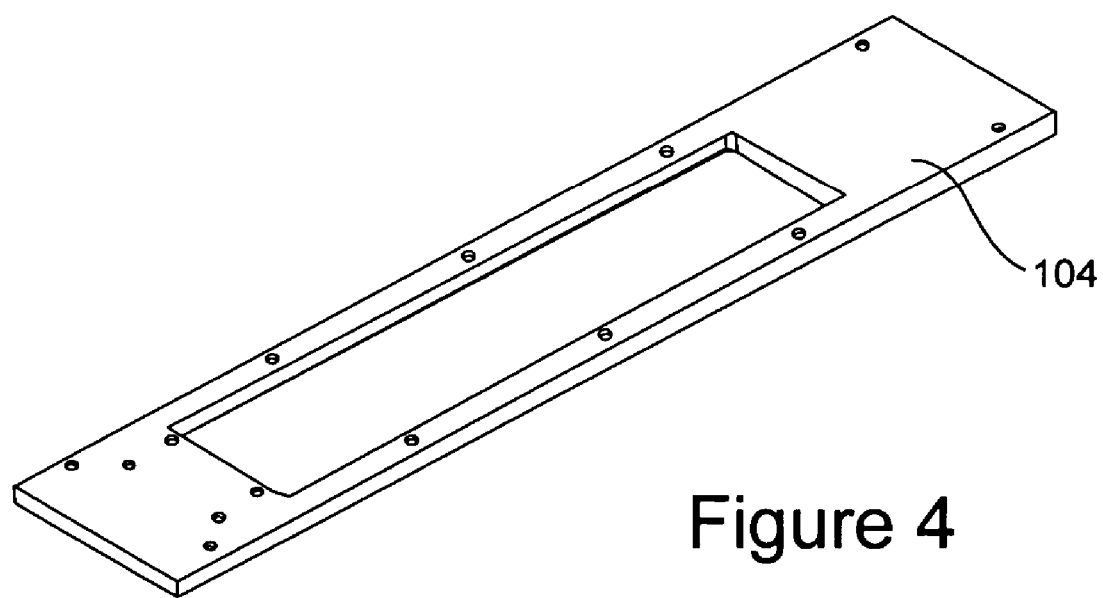
FIG. 4 shows a perspective view of a bottom plate of the canister of FIG. 3.
Figure 5:
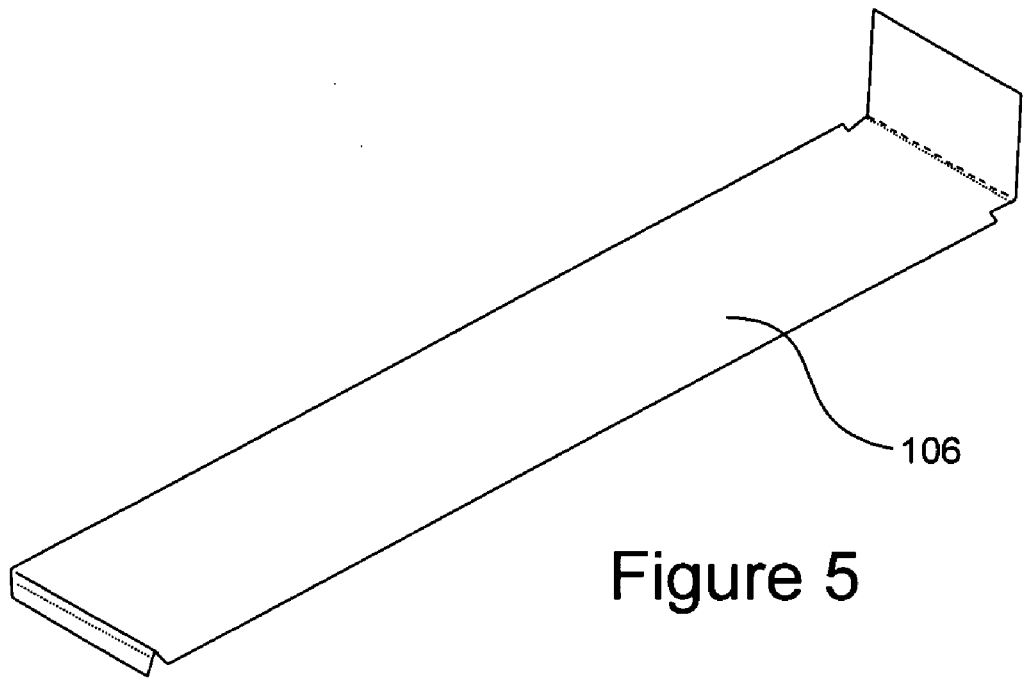
FIG. 5 shows a perspective view of a door of the canister of FIG. 3.
Figure 6:
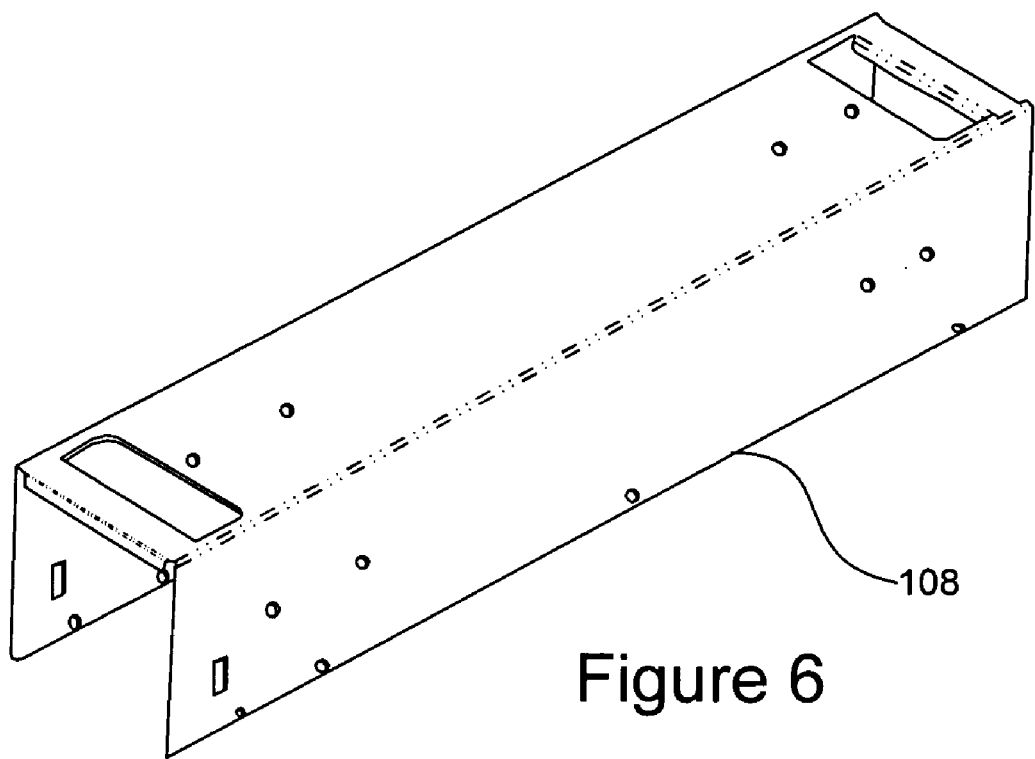
FIG. 6 shows a perspective view of a top of the canister of FIG. 3.

Canister 102 is shown in FIGS. 1 and 2, and in isolation in FIG. 3. FIGS. 4, 5, and 6 show a bottom plate 104, a door 106, and a top 108, respectively, of canister 102. The canister and the automatic dispensing system can be any of a variety of sizes so that the instant invention is able to dispense many or a few tablets into vials/trays. Canister 102 is a housing container for tablets, or other forms of drug product. Canister 102 includes a door 106 with a manually-applied tamper evident security strap (not shown) with a unique barcode. If door 106 is opened before scanning, the seal is broken and tampering is evident to personnel. A permanent barcode serial number tag (not shown), which is a unique barcode found on each canister, is displayed on the top of the canister. A permanent visual number tag (not shown), which is a visually readable number on each canister, is also displayed on the top of the canister. A security identification chip, embedded within the canister, provides a unique electronic signature to the central computer system. The ID chip cannot be altered or reprogrammed enabling a very secure barcode validation by the central computer.

The design of the canister ensures that all the tablets transfer into the counter successfully. Canister door 106 forms the entire bottom of the chamber containing the drug product. With no edges or lips to trap even the smallest tablets, complete transfer is achieved via gravity alone without the use of vibratory or other mechanical methods.

Figure 7:
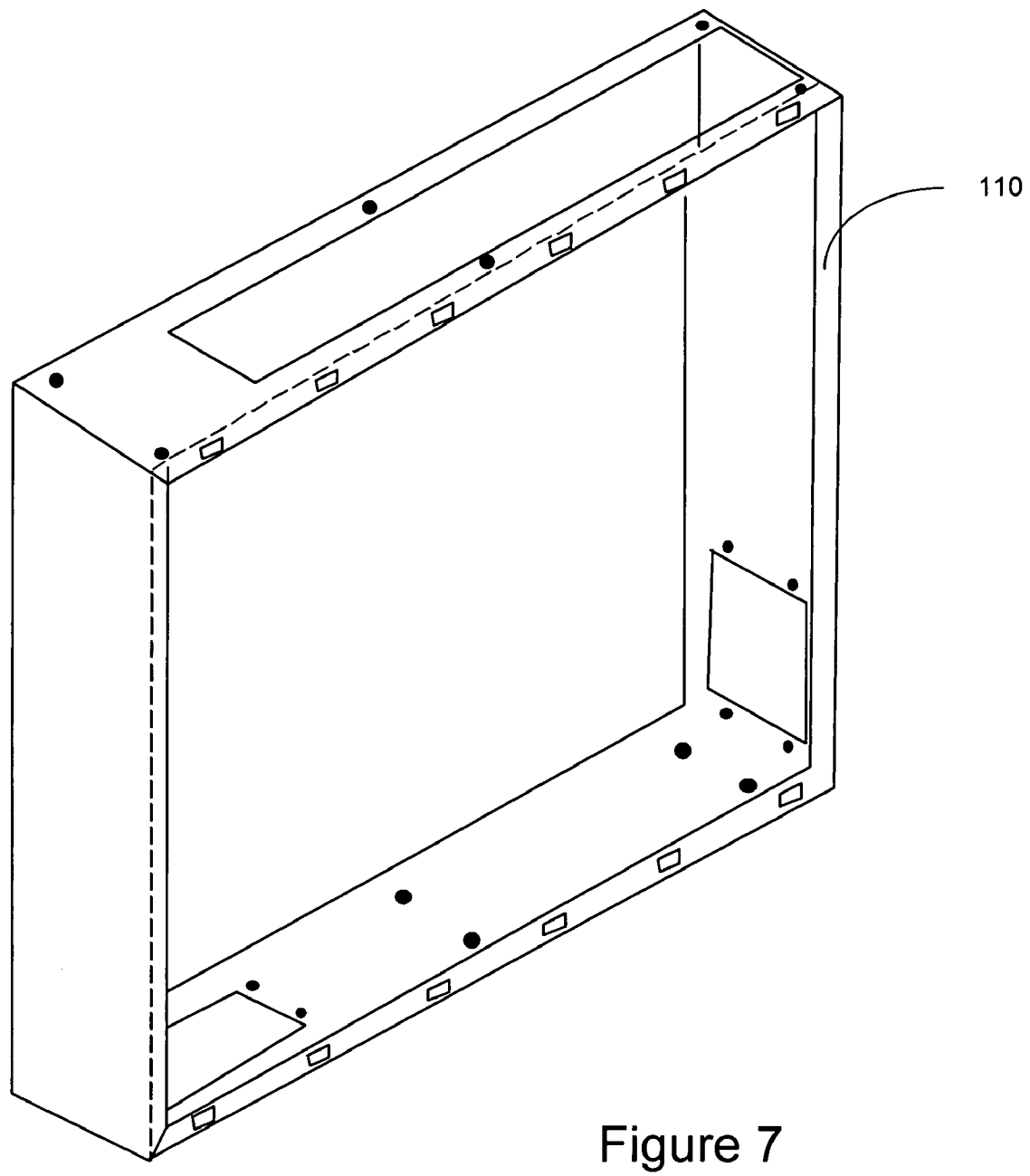
FIG. 7 shows a perspective view of a main enclosure of a counter of the automated tablet dispensing system of FIG. 1.
Figure 8:
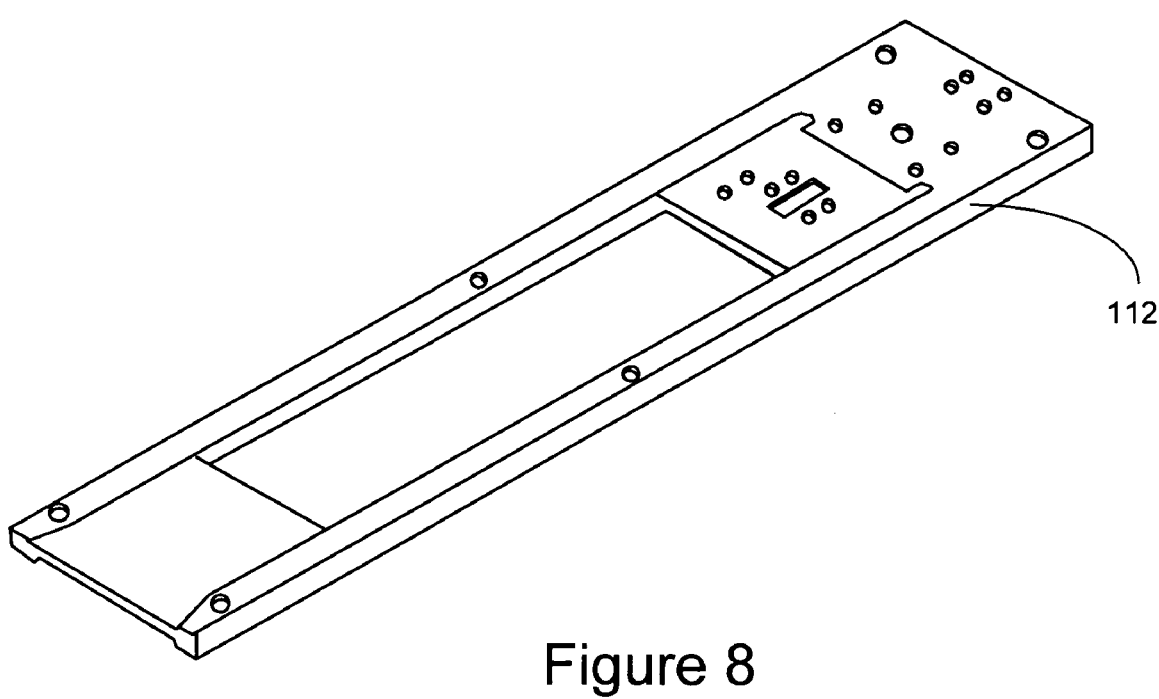
FIG. 8 shows a perspective view of a top plate of a counter of the automated tablet dispensing system of FIG. 1.

A main enclosure 110 of counter 109 is shown in FIG. 7, and a top plate 112 of counter 109 is shown in FIG. 8. Counter 109 includes all of the components inside main enclosure 110, as best seen in FIGS. 1 and 2, including hopper assembly 114, sensor 126, control board 132, and buffer assembly 128. In a preferred embodiment, the counter has a computer board that allows the counter to have adjustable speeds in counting tablets and can also perform diagnostic tests on the counter(s). The automatic dispensing system may contain a plethora of counters that allow the simultaneous counting of tablets. Although not shown in the drawings, the counter includes a unique and permanent barcode serial number tag and permanent visual number tag on its front plate. The counter or counters also optionally contain a RF chip or another means of identifying the counter(s) for security purposes to insure that the counter(s) is/are at the correct system location. This identification device ensures that the vials/trays get filled with the proper tablets and also optionally makes the counter(s)

tamper proof so that the tablets are not being accessed by unauthorized personnel. The security identification chip, embedded within the counter, provides a unique electronic signature to the central computer system. The ID chip cannot be altered or reprogrammed enabling a very secure barcode validation by the central computer. Counter 109 includes an integrated top door with an automated locking mechanism. Top docking plate 112 of counter 109 receives the corresponding canister. The counter top door (not shown) remains closed and locked until a proper canister is attached to top docking plate 112 of counter 109 and verification scanning is successfully completed by scanning the barcodes on canister 102 and counter 109, as well as the security tag and electronic validation of the barcodes via the embedded ID chips. The counter door is unlocked automatically if the scanned codes match information stored in a central database. The counter door is required to be opened first, then canister door 106 is opened. Once the counter and canister doors are opened, drug product empties from the canister into the counter. In one embodiment, the counter has a capacity of about 2000-2500 cubic centimeters.

A large side door (not shown) is included on counter 109 for cleaning purposes, and preferably may only be opened with a special tool. The counter can be taken out of its shelf docking location for cleaning. Once removed, the counter is taken to a separate room and placed into a cleaning docking station for cleaning. The large side door of the counter is removed, and the counter is cleaned according to instructions. The door is replaced and the counter is returned to its independent shelf location and placed into its assigned shelf docking station, where the central computer validates and activates the counter.

In one embodiment, the enclosure 110, as seen in FIG. 7, can serve the function of making the ATD a closed unit so that no particles or dust enter or depart the ATD. Moreover, if the enclosure is a closed unit, the risk of cross contamination and unauthorized personnel from accessing the product is prevented. In one embodiment, the inside of the enclosure can be accessed through a side cover that is attached with security screws, wherein the security screws are there to prevent tampering.

Figure 9:
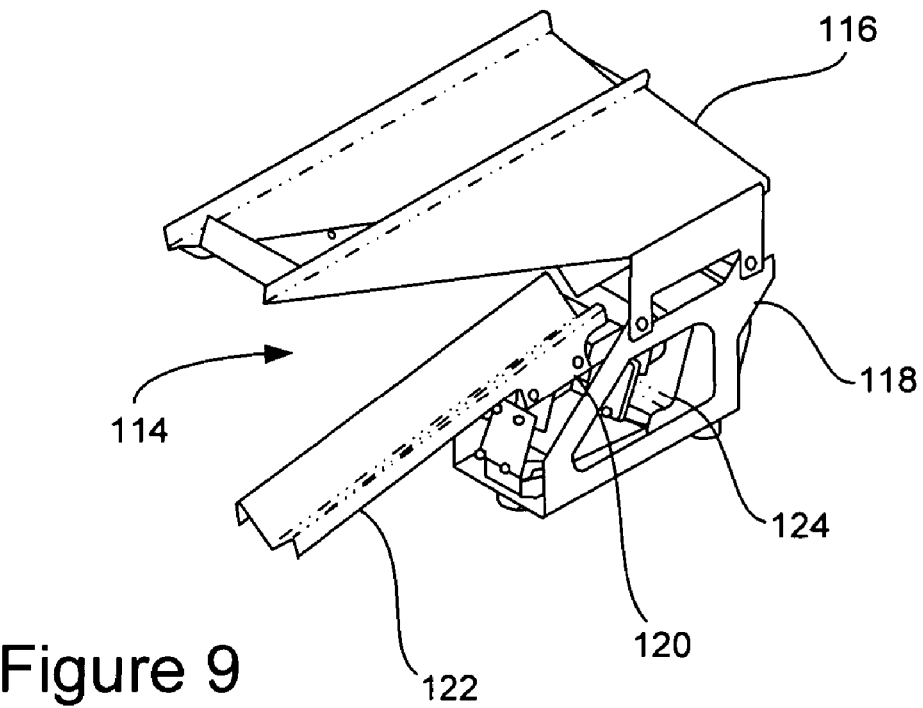
FIG. 9 shows a perspective view of a hopper assembly including the dispenser reserve, singulation channels, and vibrating feeder of the automated tablet dispensing system shown in FIG. 1.
Figure 10:
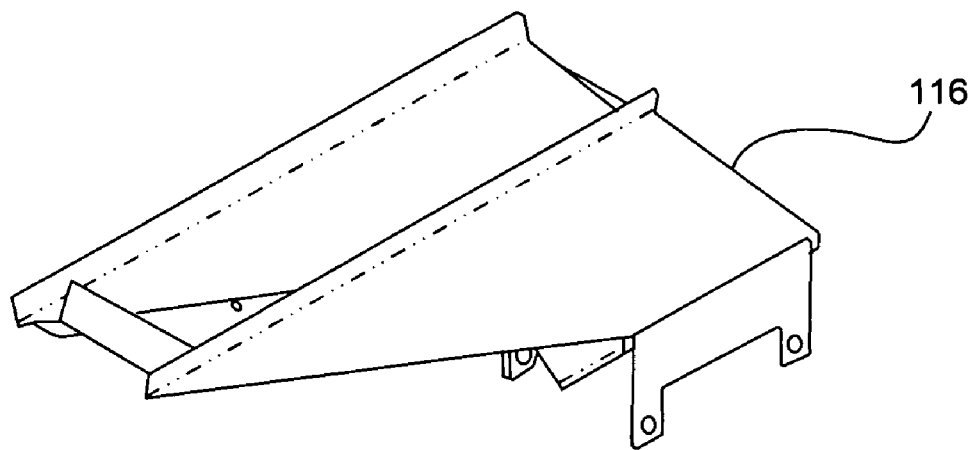
FIG. 10 shows a perspective view of a dispenser reserve of the hopper assembly of FIG. 9.
Figure 11:
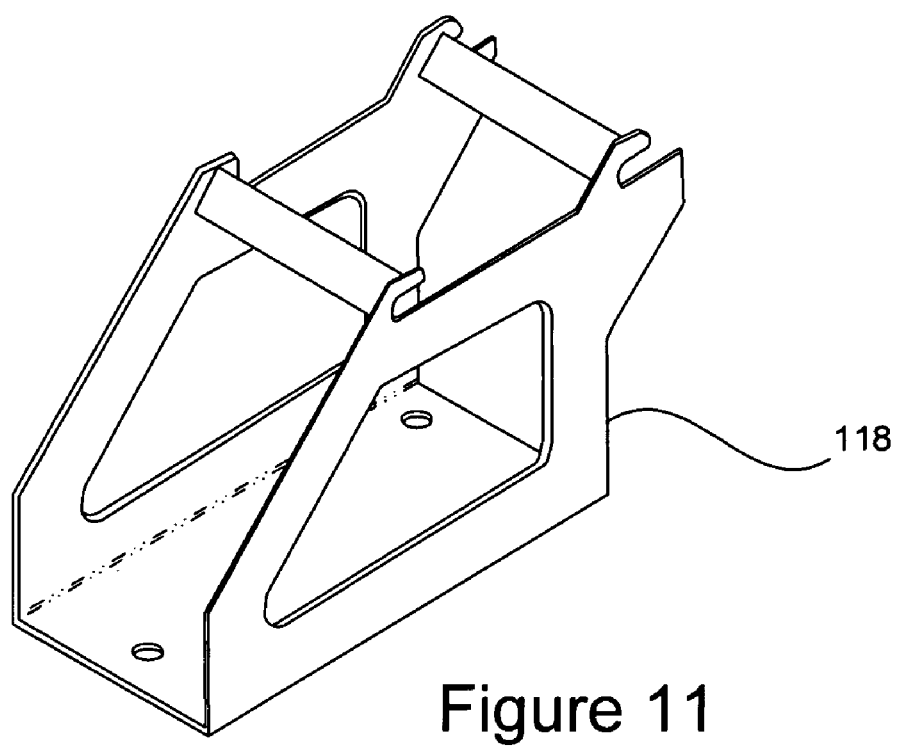
FIG. 11 shows a perspective view of a hopper support of the hopper assembly of FIG. 9.
Figure 12:
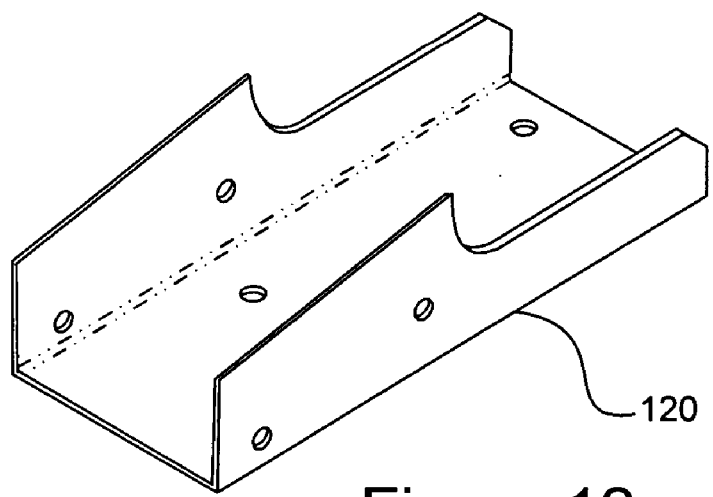
FIG. 12 shows a perspective view of a singulation channel support of the hopper assembly of FIG. 9.
Figure 13:
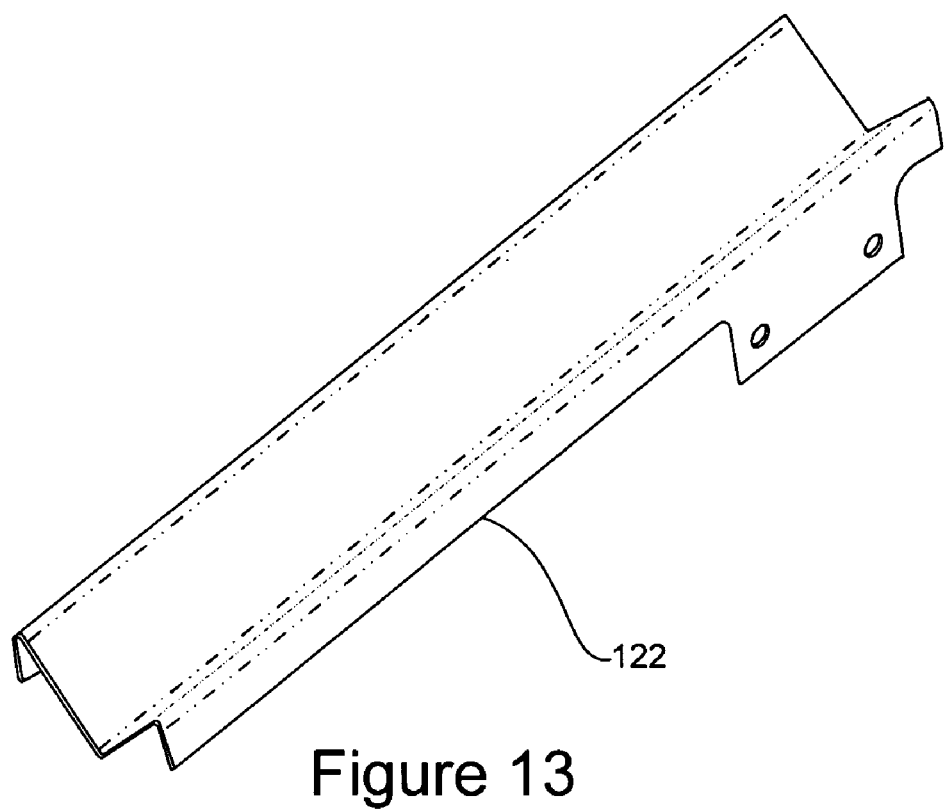
FIG. 13 shows a perspective view of a singulation channel of the hopper assembly of FIG. 9.
Figure 14:
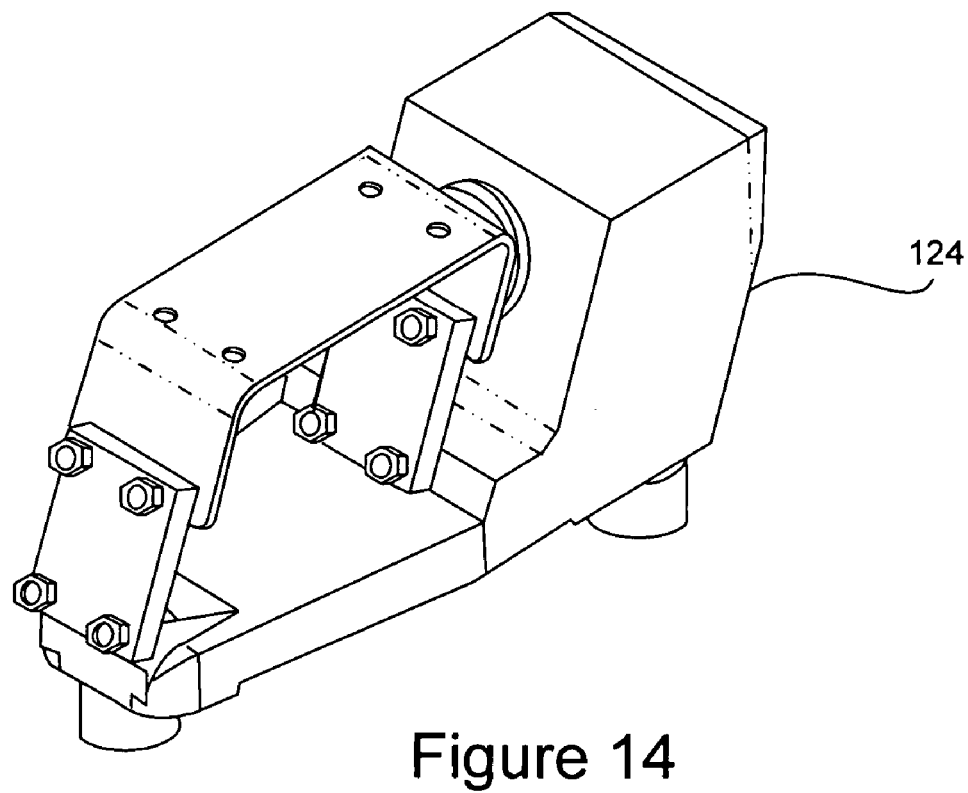
FIG. 14 shows a perspective view of a vibrator of the hopper assembly of FIG. 9.
Figure 15:
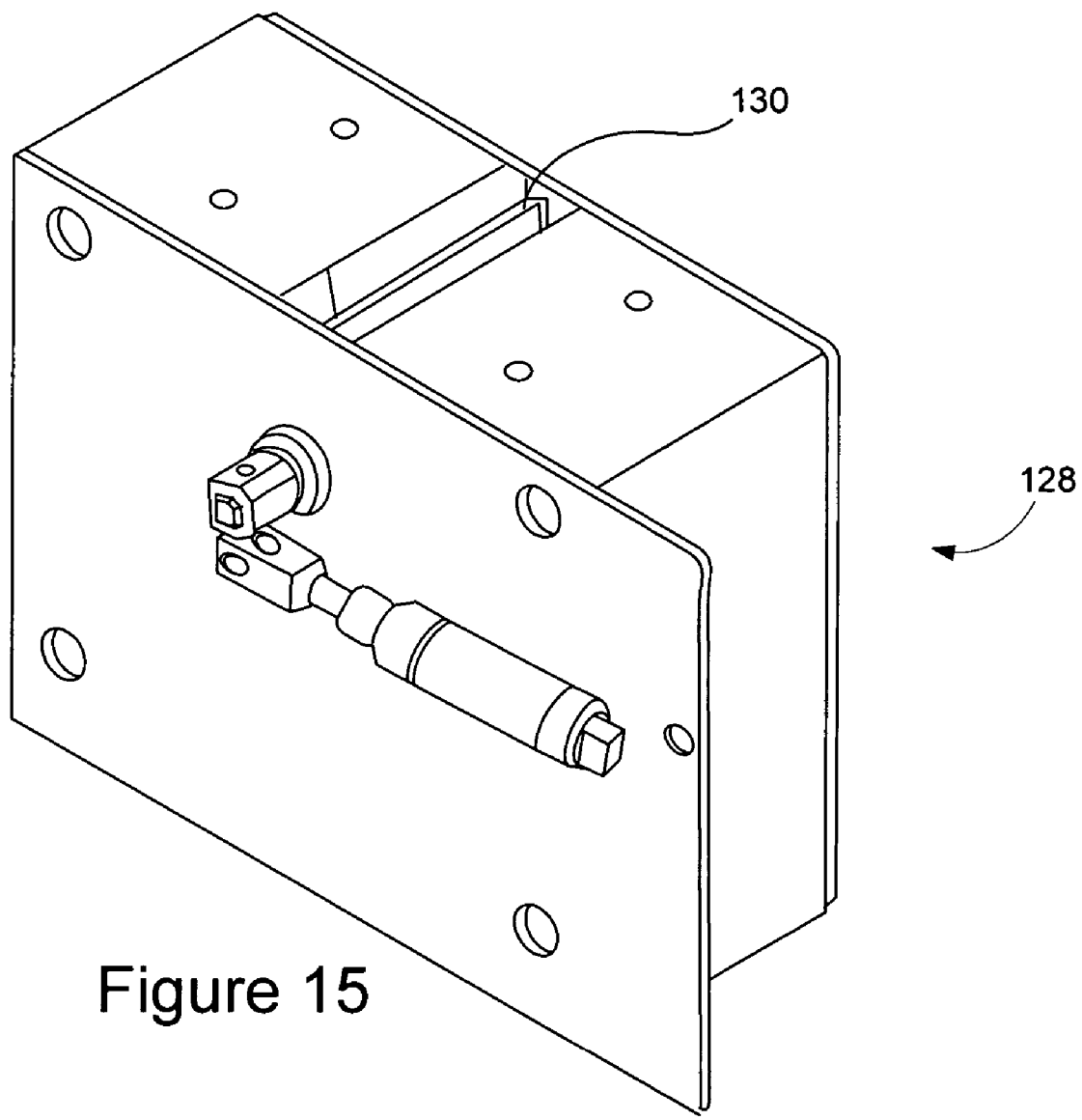
FIG. 15 shows a perspective front view of a buffer of the automated tablet dispensing system of FIG. 1.
Figure 16:
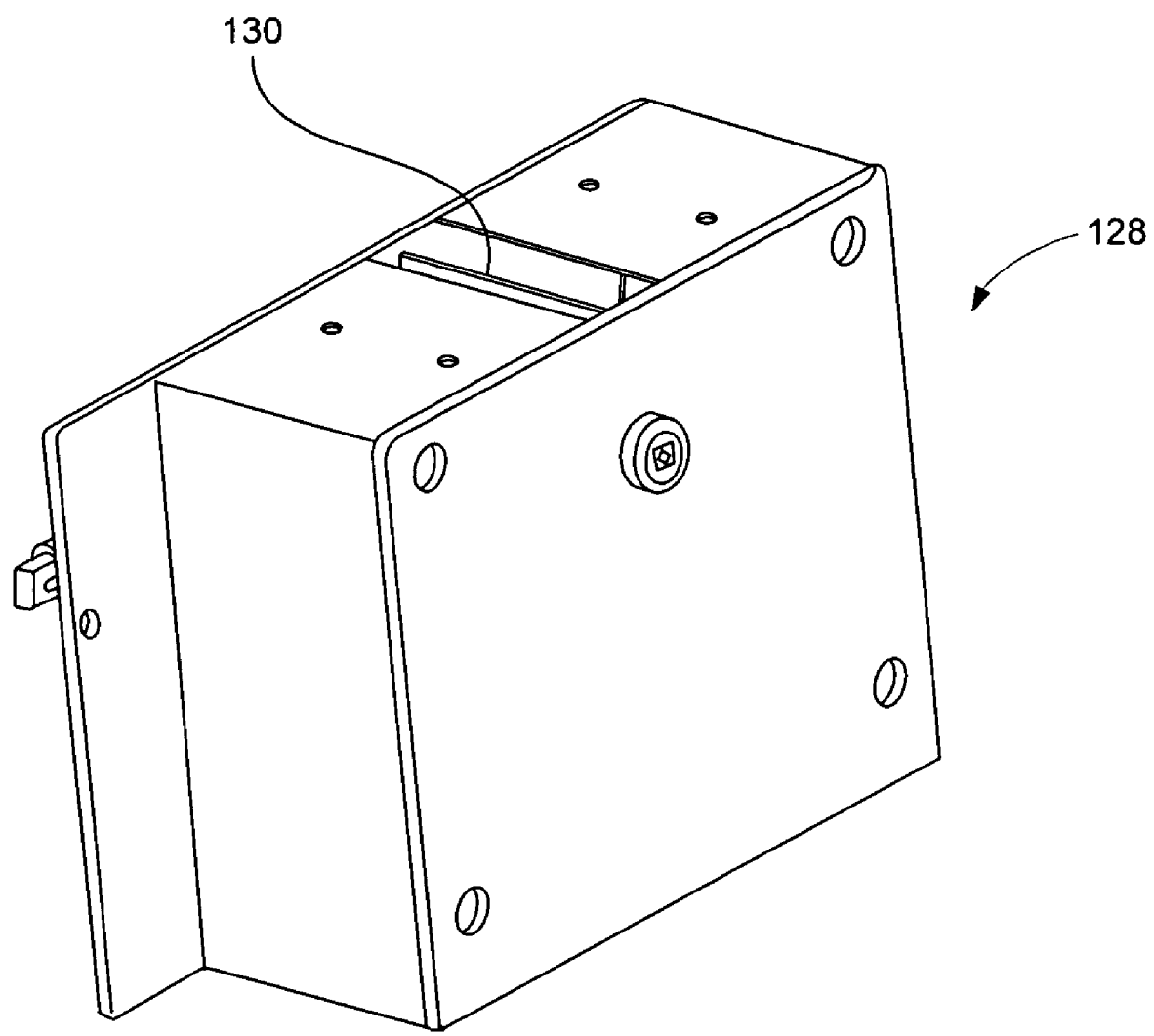
FIG. 16 shows a perspective rear view of a buffer of the buffer of FIG. 15.

Hopper assembly 114, shown in FIG. 9, is included in counter 109 for product storage and feeding of tablets through the scanning system. The hopper assembly includes dispenser reserve 116, singulation channels 122, and vibrating feeder 124 as shown in FIG. 1. Some portions of hopper assembly 114 are shown in isolation in FIGS. 10-14. FIG. 10 shows dispenser reserve or hopper shell 116, FIG. 11 shows a hopper support 118, FIG. 12 shows a singulation channel support 120, FIG. 13 shows singulation channel 122, and FIG. 14 shows vibrator 124. As drug product empties from canister 102 into counter 109, the tablets are fed into dispenser reserve 116 of hopper assembly 114. Vibrator 124 assists in moving the product from reserve 116, down singulation channel 122 toward sensor 126.

In one embodiment, the hopper may contain approximately 2000 cc of product, although other amounts are contemplated and possible, such as amounts like 100 cc to 2500 cc product. A vibratory drive may move the product from the hopper to the sensor while spreading and isolating each tablet as it slides along the singulation channel. In one embodiment the hopper and vibratory drive are balanced so that tablets flow at a constant rate. It is contemplated that the hopper and vibratory drive can be balanced by computer control so that fine tuning occurs automatically.

Sensor 126, with its location shown only in FIGS. 1 and 2, is present inside counter 109 to count tablets. In a preferred embodiment, the technology used for the sensor is not dependent on the type of tablet being counted, can identify an incorrect or broken tablet, and is immune to dust created by movement of the tablets from the canister through the hopper. Moreover, there is a sufficiently wide channel so that dust does not affect counting. Sensor 126 is preferably an electrostatic field scanner, such as that described in U.S. Pat. No. 6,504,387, issued to Shail et al., entitled "Item Detection/Inspection Arrangement", which is hereby incorporated by reference in its entirety or that manufactured by Sparc Systems Ltd. of Malvern, Worcestershire, United Kingdom. An infrared spectroscopy sensing device, such as that manufactured by Foss NIR Systems, Inc. of Silver Spring, Md., U.S.A., may also be used. If dust immunity is not an issue, a light barrier type sensor, such as that manufactured by Banner Engineering Corp. of Minneapolis, Minn., U.S.A., may be employed. Another sensor that is contemplated is a SICK detector. Those skilled in the art understand that, whatever the sensing technology utilized, adaptations are typically required for successful implementation into a particular automated tablet dispensing system.

Figure 17:
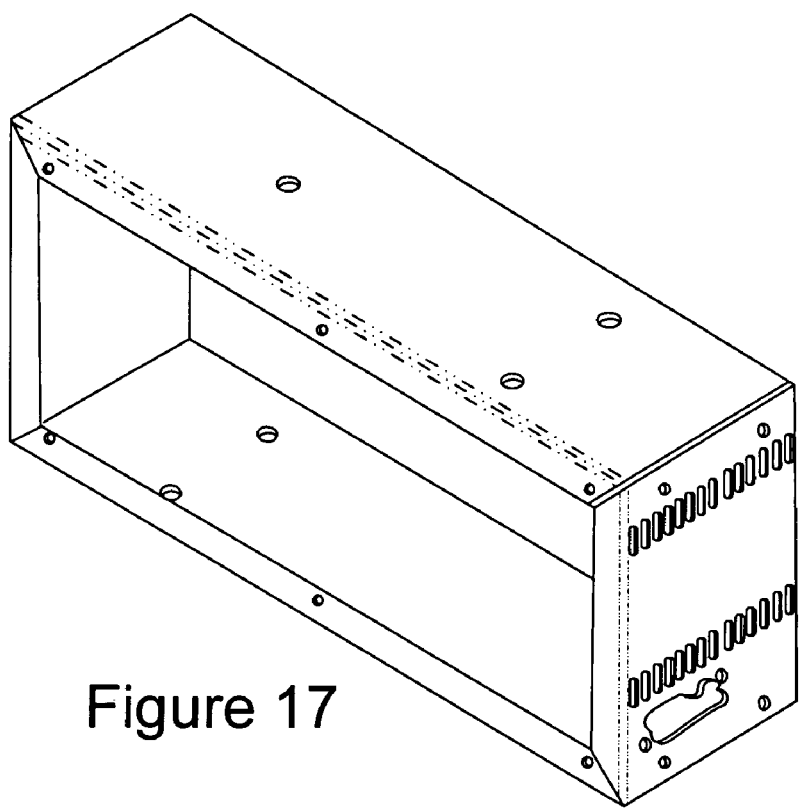
FIG. 17 shows a perspective view of a control box of the automated tablet dispensing system of FIG. 1.
Figure 18:
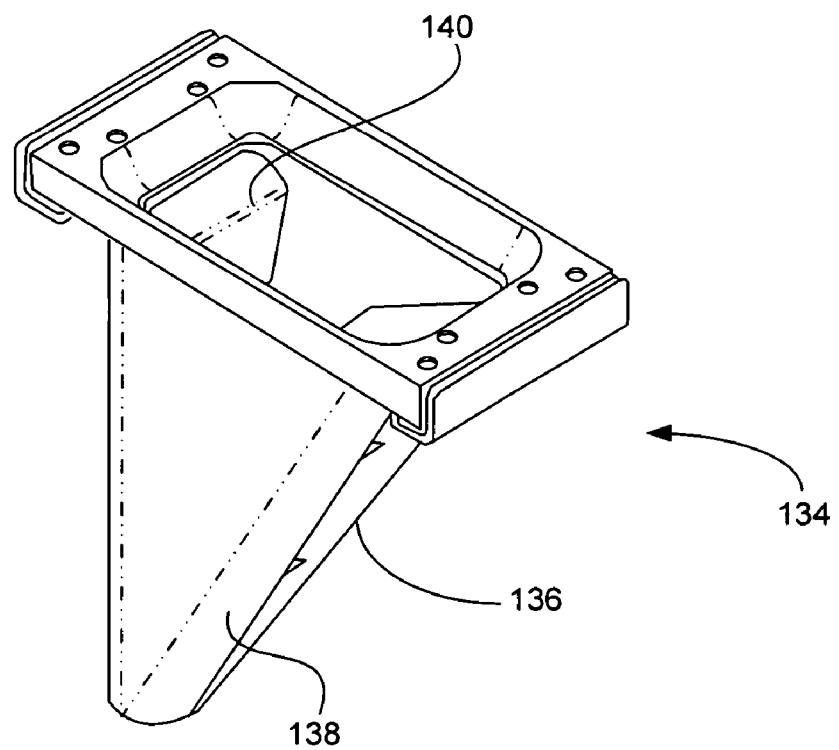
FIG. 18 shows a perspective view of a nozzle assembly of the automated tablet dispensing system of FIG. 1.
Figure 19:
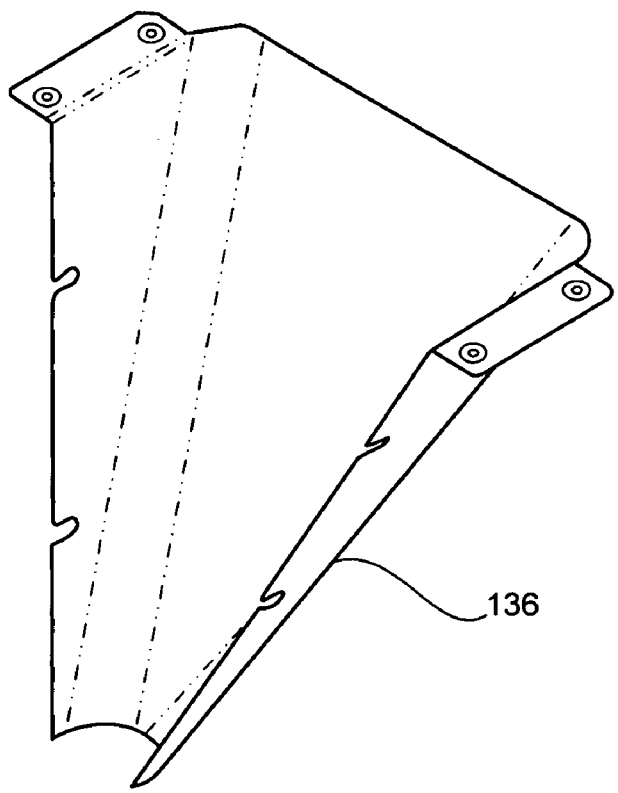
FIG. 19 shows a perspective view of a fixed nozzle of the nozzle assembly of FIG. 18.
Figure 20:
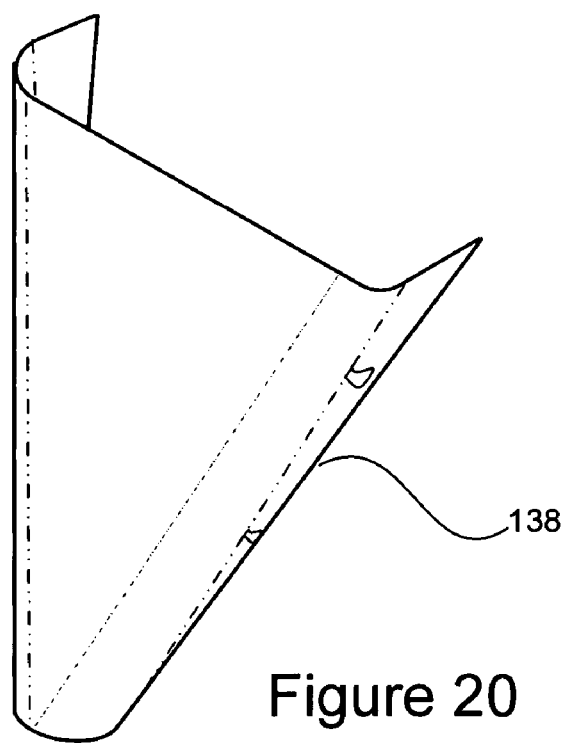
FIG. 20 shows a perspective view of a removable nozzle of the nozzle assembly of FIG. 18.
Figure 21:
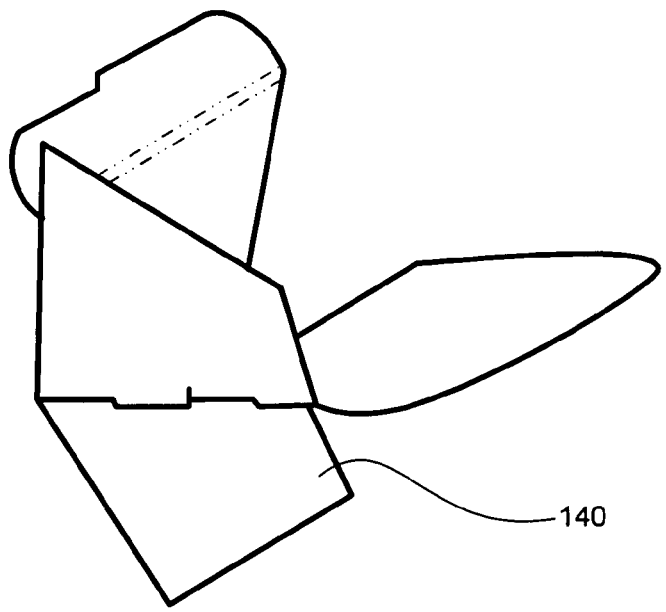
FIG. 21 shows a perspective view of a nozzle baffle of the nozzle assembly of FIG. 18.

Buffer assembly 128 of counter 109 is shown in FIGS. 1, 2, 15, and 16. Buffer assembly 128 includes an automated flipper door 130 to hold pre-counted tablets before filling into vials, bottles, trays (with plastic trays being preferred) or similar containers through the nozzle assembly. Nozzle assembly 134 is shown in FIG. 18. A fixed portion 136 of nozzle assembly 134 is shown in FIG. 19, while a removable portion 138 of nozzle assembly 134 is shown in FIG. 20. The removability of portion 138 shown in FIG. 20 provides the ability to thoroughly clean the system. A nozzle baffle 140 of assembly 134 is used to prevent bridging and is shown in FIG. 21. Electronic counter control board enclosure or box 132, shown in FIG. 17, is also included.

The nozzle is designed so that tablets do not get jammed or blocked. In one embodiment, this is accomplished by inserting an internal deflector so that tablets pass through the nozzle easily. In one embodiment, the deflector can be disassembled for easy cleaning of the deflector and the nozzle. Moreover, in one embodiment, the nozzle is designed to ensure smooth product transfer. This is generally accomplished by making the nozzle design adjustable in different directions so that the nozzle can accommodate different size tablets and different size vial/tray openings. The adjustable nozzle provides the advantage of reducing spillage of the product.

One advantage to the instant invention is that a computer based system allows the automatic calibration of the system to accommodate any of a variety of tablet sizes, even tablets that have not previously been counted. To Applicants knowledge, the instant invention is the first system to have this ability as all previously known systems require time-consuming calibration (usually performed manually) and expensive new components to accommodate different tablet sizes.

In one embodiment, the buffer is designed so as to hold one order at a time. However, it should be understood that alternative designs are contemplated that can contain more than one order at any time. For example, one embodiment of the buffer encompasses a two-buffer chamber that allows a vial or bottle to be present and discharged to the vial or bottle. The buffer allows the holding of tablets prior to the arrival of a puck containing a vial. As soon as the vial arrives the buffer can dispense tablets and pre-count tablets for the next or any subsequent order. In one embodiment, the side of the buffer is a stainless steel plate that holds a pneumatic cylinder to actuate the system. In an exemplary embodiment, the side plate can be easily removed for cleaning the inside of the buffer.

The design of buffer assembly 128 allows pre-counting of tablets before a vial is filled thus increasing throughput. One embodiment of a buffer assembly has two compartments with a flipper door. However, it should be understood that multiple compartments are possible and contemplated. In a preferred embodiment, the capacity per compartment is about 180 cubic centimeters, although it is contemplated that other sizes can be accommodated. After a prescription order is entered into the computer system, the appropriate counter may begin counting product into its buffer. In most cases, the transition time of the empty vial between its holding position and the counter is sufficient to allow completion of the counting process. Thus, when the vial arrives at the assigned counter, the product can be dispensed rapidly into the vial, and the vial can be conveyed forward to final inspection and shipping. Furthermore, the buffer enables intelligent exception handling. In the case where an individual counter exhausts its dispenser reserve prior to completing an order, the partially filled vial can be rerouted to another counter, containing the same drug product, which will dispense only the amount of drug product necessary to complete the order.

In an embodiment, the electronics for the system, including a control board, one or more pneumatic valves, and a power supply may be located inside an enclosure that protects them from dust or product. A vent at the back of this electronics enclosure allows the flow of air, so that the electronics can operate safely and reliably.

In utilizing certain embodiments of automated tablet dispensing systems of this invention, two types of human operators may be associated with refilling canisters and refilling counters by changing empty canisters. A pharmacist is in charge of refilling canisters, while a replenishment technician is in charge of refilling counters by changing empty canisters. Alternatively, a robot can be used instead of a replenishment technician. All persons with access to the canisters have a unique barcode personal identification. These unique barcode IDs are used by the central computer to authorize an operator to perform tasks and to record who is in possession of the canister and drug product at all times. The canisters are handed from person to person and a wireless RF (radio frequency) gun, which is a barcode scanner used to input information from barcodes into a central database, is used to record the transfer of the contents in a central database for tracking and security purposes. The barcode scanning and other security measures described in this paragraph and other paragraphs herein provide a high level of security and full tracking of canisters and drug product.

A pharmacist is located in a secure room. The pharmacist receives empty canisters and fills them with the appropriate drug from bulk. A bulk bottle or container is where tablets of a particular drug are commonly stored before refilling the canisters. Each time a canister is refilled, a unique refill identification number is created and stored in a database to track the product. The unique refill ID number is preferably the barcode located on a tamper evident seal, which is a disposable plastic strap that is destroyed when the canister is opened, and is linked to the barcode on the canister and the embedded canister ID chip number. The central computer can assign the canister to the appropriate counter and link the refill ID number to the counter barcode and embedded counter ID chip number, and the docking station barcode and embedded docking station ID chip number.

The pharmacist scans the canister barcode, his or her unique personal ID number, and the NDC (National Drug Code) barcode of the bulk bottle. The scanned information is stored in a central database with the required information for tracking and monitoring the canister and drug product flow. A replenishment technician in charge of the automated tablet dispensing system or a robot receives the filled canisters from the secure room and upon scanning of the unique refill ID number and his or her unique personal ID number, the change of possession of the canister is recorded in the central database.

Alternatively, the canister can arrive pre-filled from another location. The canisters of the present invention are designed so as to be able to ship the canisters to another location wherein the canisters can be filled with tablets in a manner similar to that performed by the pharmacist in the secure room as described above. In a preferred embodiment within this embodiment, the pre-filled canisters should have the same security precautions as those canisters that are filled by the pharmacist in the secure room (e.g. a security tag, RFIDs, etc.).

The replenishment technician or alternatively, the robot places each filled canister on top of the appropriate counter and visually verifies that the serial numbers correspond. The replenishment technician scans all barcodes to verify that the information in the central database corresponds to the units on hand. The central computer then validates that the scanned barcodes and the embedded ID chips all correlate to the refill ID number. The system then unlocks the counter door, allowing the replenishment technician to load the counter with the correct product.

An exemplary embodiment of a process for filling empty canisters in a secure room is described as follows. A pharmacist scans his or her personal ID barcode, triggering a check to ensure that the pharmacist is authorized to perform this task and time stamp the operation. The empty canister barcode is then scanned and placed into a refill docking station. The central computer then validates the canister barcode via the embedded canister ID chip. The central computer generates a work order for refilling the canister. Once the work order is received, the bulk container with tablets is retrieved, and the product identification information, lot number, expiration date, and quantity are scanned in (or may be manually entered) using a wireless RF gun or similar means. Each time information is scanned, it is stored in the central database. The canister door is opened, and the canister is filled with tablets. The door of the canister is then closed, and the security seal with barcode is attached to the canister. The canister, security seal and personal ID barcodes are scanned, and a finish time stamp is recorded in the central database. The sealed canister is removed from the refill docking station, and the refill process is complete.

An exemplary embodiment of a process for placing a filled canister onto the appropriate counter is described as follows. A replenishment technician scans the replenishment technician's ID barcode, triggering an authorization process and time stamp. The canister is received from the secure room. An intact security seal and visually readable canister number tag are verified via barcode scanning. The canister is brought to and docked with the appropriate counter. The canister, counter, and docking station barcodes are verified by scanning and validated via the embedded ID chips. Once all of these are verified as correct by comparison to information in the central database, a message is transmitted to the replenishment technician that the security seal on the canister may be destroyed.

The system automatically opens the security locking mechanism of the counter door. The doors of the counter and the canister are then manually or alternatively, automatically opened, allowing transfer of drug product into the counter. After completion of transfer of the product into the counter, a message is generated instructing closure of the counter door.

Once the door is closed, the security mechanism automatically locks the door. The canister door is then closed, and the canister may be removed from the counter and taken to the refill station once again.

In certain exemplary embodiments of some of the processes described herein, all processes are time stamped and have to be performed within certain user definable time windows. If an operation is not completed in a timely manner, a time out occurs, triggering automatic dispatch of an authorized supervisor to the location to verify the reason of the event. The process may be re-started or continued only if the supervisor gives authorization to continue.

Figure 22:
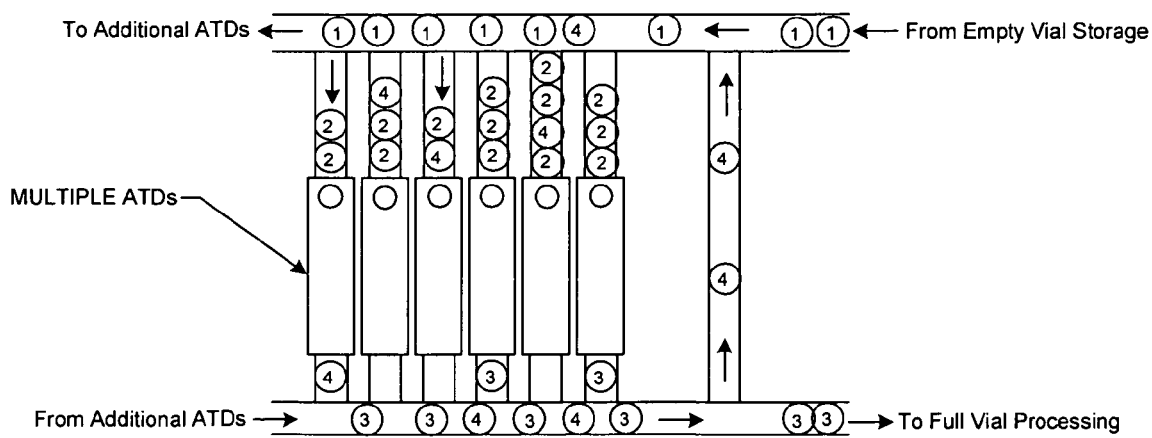
FIG. 22 shows a schematic plan view of an exemplary embodiment of a prescription filling system according to this invention.
Figure 23A:
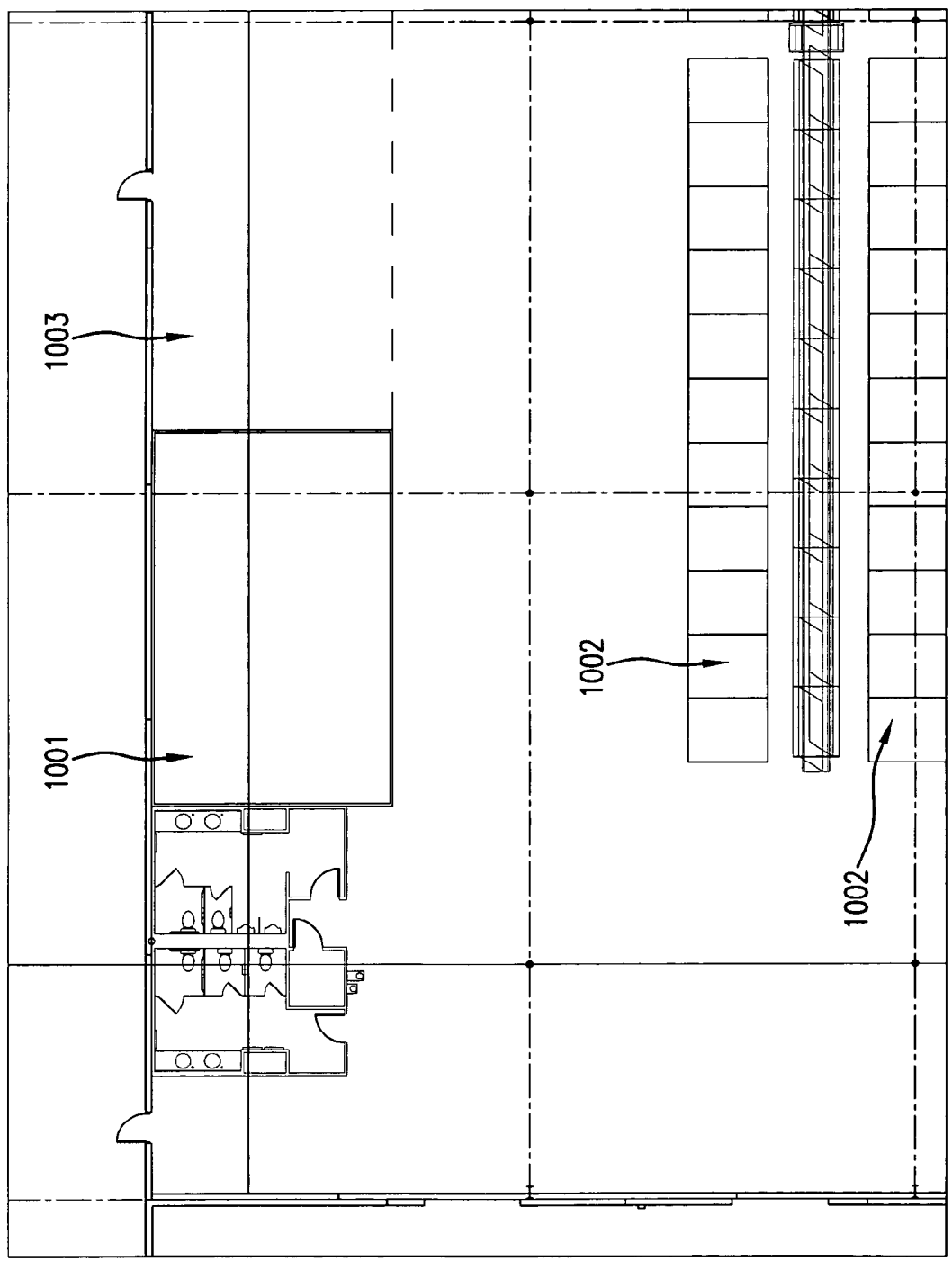
FIGS. 23A-23F show an exemplary embodiment of a prescription filling and patient order packaging system according to this invention.
Figure 23B:
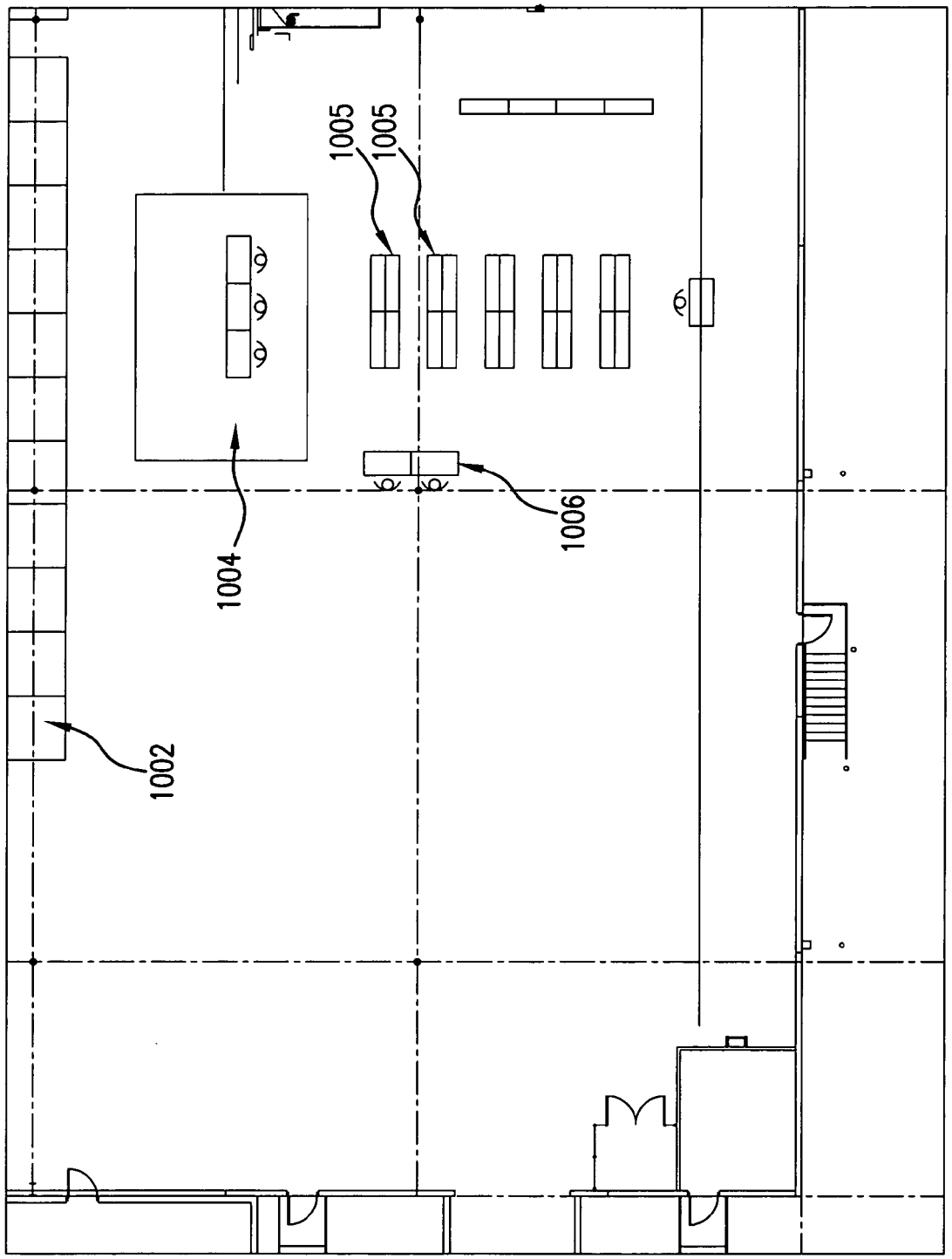
Figure 23C:
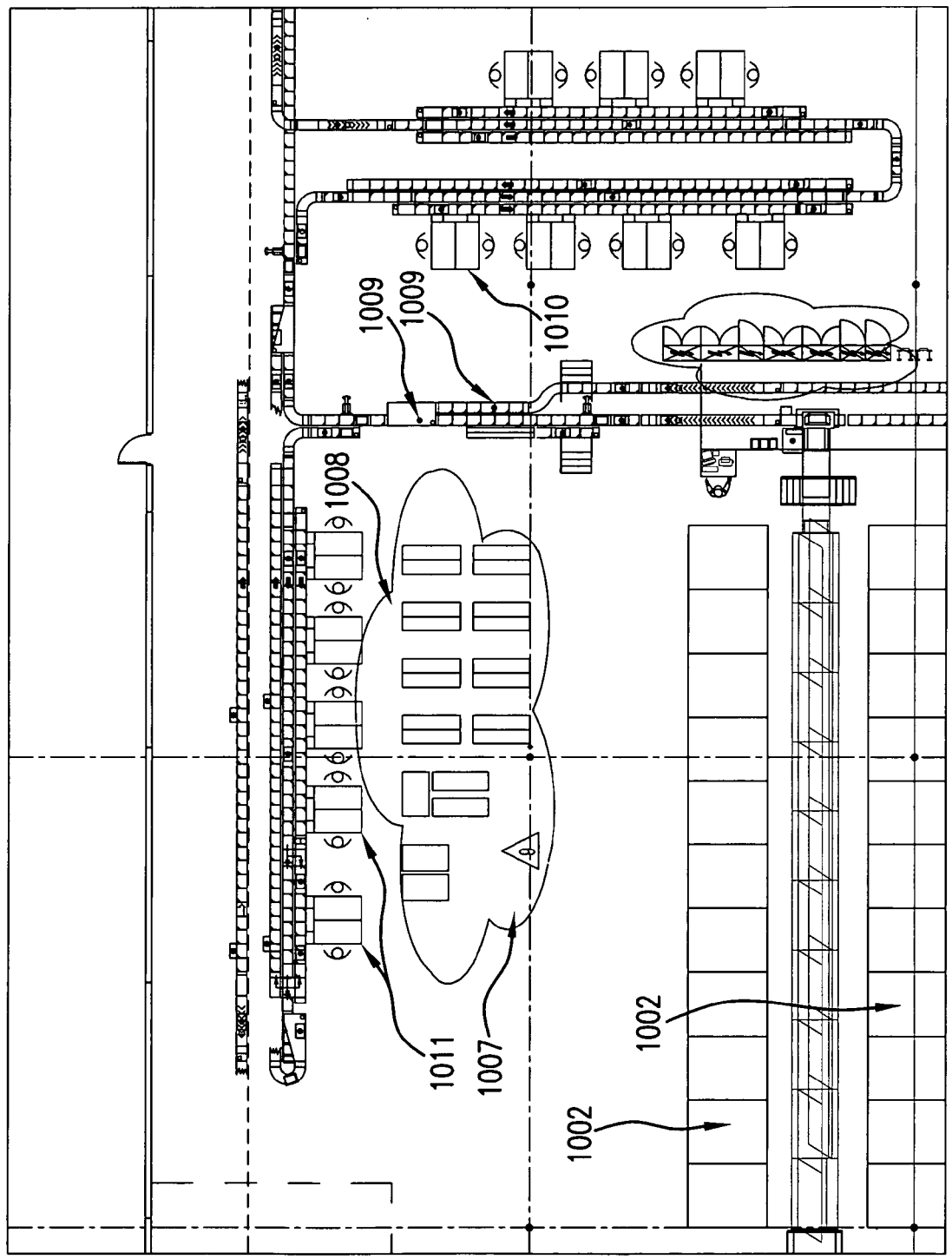
Figure 23D:
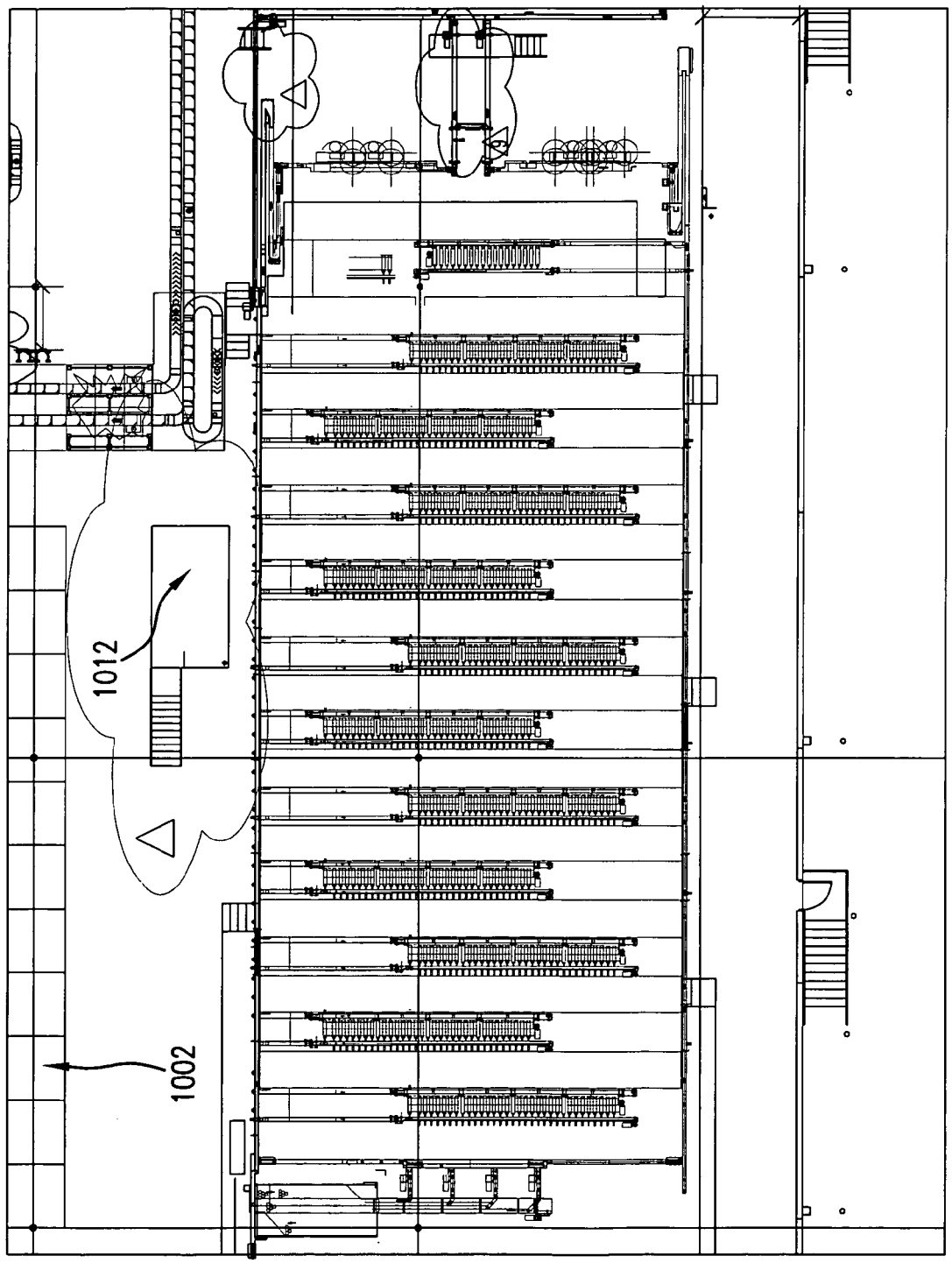
Figure 23E:
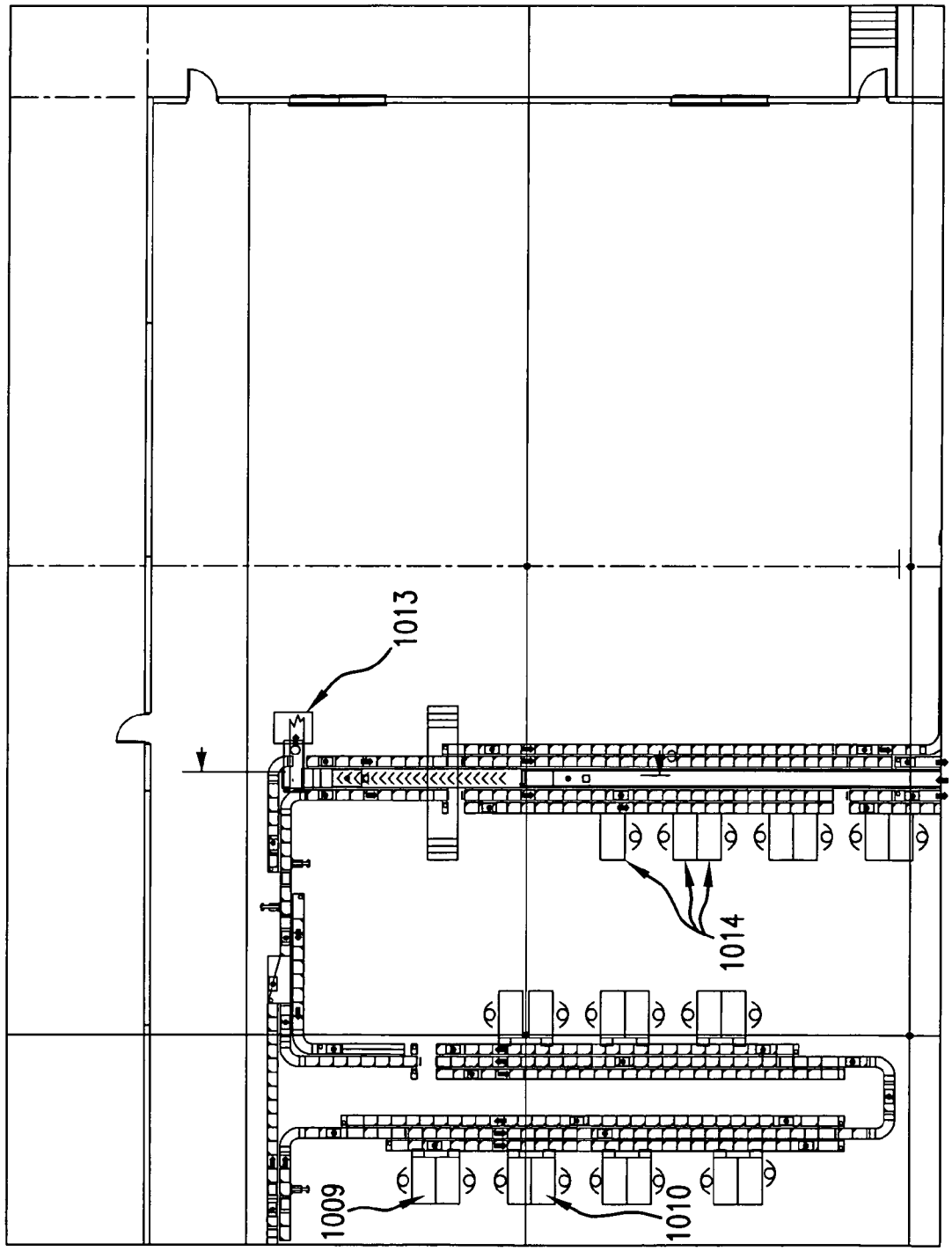
Figure 23F:
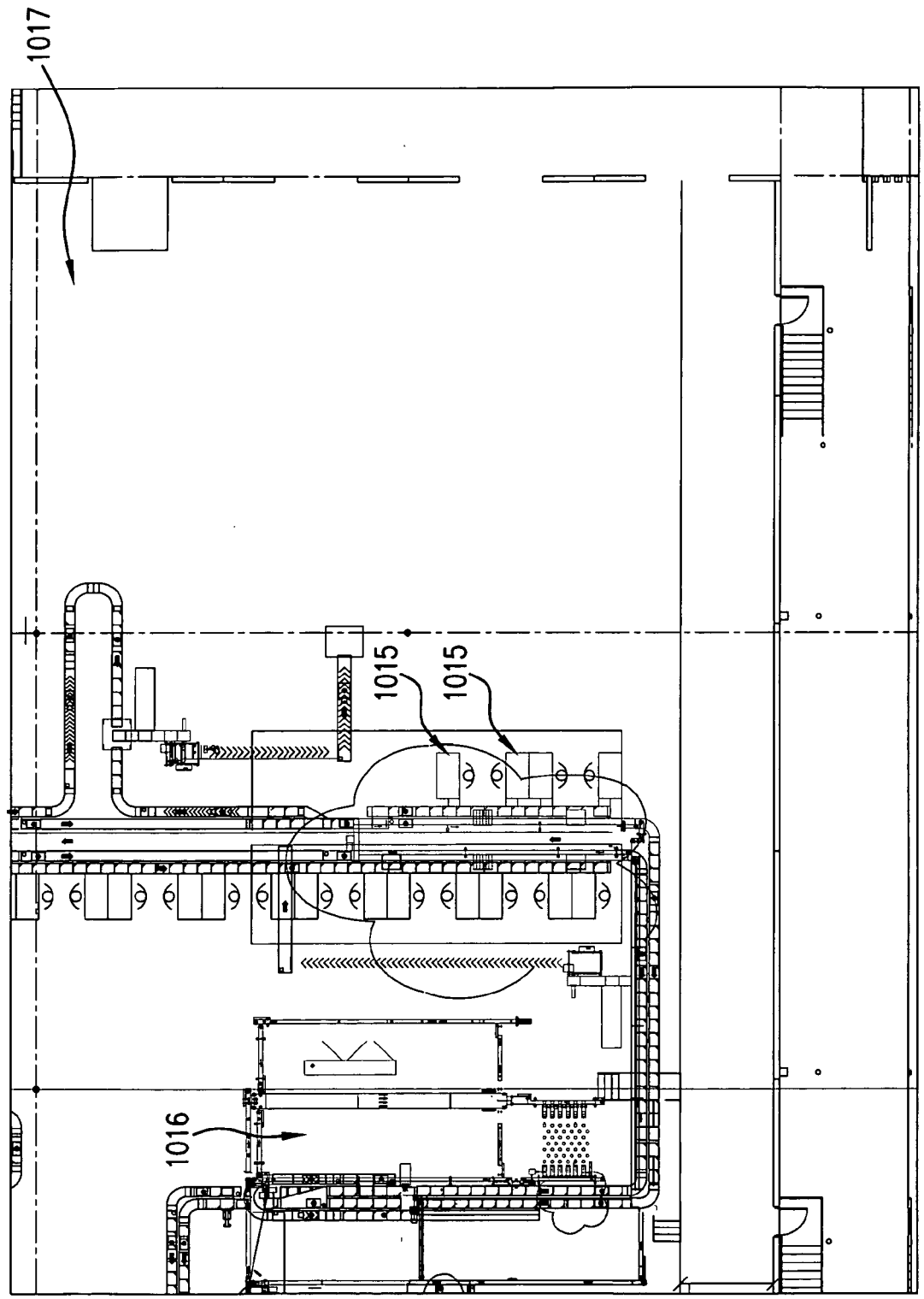

An exemplary embodiment of a prescription filling system according to this invention includes a vial conveyor matrix with a plurality of automated tablet dispensing systems, a portion of which is shown in FIG. 22. Empty vials are moved along a conveyor from their storage area to the appropriate automated tablet dispensing system (ATD). Multiple vials representing multiple orders are provided with a queuing location adjacent to their appropriate ATD as shown. After filling, each vial moves along a conveyor to a final processing area. Full vials proceed to an area where they may be reviewed by a human operator, capped, and packaged with vials for the same patient. Pre-packaged goods/items may also be included in the final package that is labeled and shipped to the patient. Rather than being reviewed by a human operator, capped, and packaged for shipment, partially filled vials return via conveyor to the matrix of ATDs to be completely filled according to the patient's order. This may occur, for example, if a prescription order is for 30 tablets of a particular drug and the ATD only has twenty remaining tablets. The partially filled vial may be sent to another ATD that contains the same drug to receive the final 10 tablets needed. Although the matrix shown in FIG. 22 shows only six ATDs, it should be understood that a prescription filling matrix may include a large plurality of ATDs, tens, hundreds, or more, such that more than one ATD may have the same type of drug. The use of numerous ATDs allows for parallel processing of prescription orders, in contrast to the serial processing that is presently common in the industry. FIGS. 23A-23F show an exemplary embodiment of a prescription filling and patient order packaging system according to this invention in detail. FIGS. 27A-27F show an exemplary embodiment of a prescription filling and patient order packaging system according to this invention in detail.

In FIGS. 23A-23F, the numbers in these figures correspond to the following: 1001 shows a security cage (fully enclosed wire), 1002 shows replenishment flow racks, 1003 shows a bulk storage processing area, 1004 shows a restricted access area wherein canister replenishment occurs, 1005 shows a canister replenishment area and a maintenance station, 1006 shows 2000 cc filling stations, 1007 shows an area where five refrigerators are, 1008 shows a manual picking and labeling area, 1009 shows where super totes are prepared, 1010 shows where specialty totes are prepared, 1011 shows where order verification occurs, 1012 shows a computer room, 1013 shows a mail sort area, 1014 shows where picking occurs, 1015 shows a tote packaging area, 1016 shows a recirculating loop, and 1017 shows a packing area.

In FIG. 24, 1 shows a toggle clamp, which locks each dispenser to the subframe, 2 shows a banner, which identifies each slot on the mezzanine, 3 shows an interface box cable terminations for power and communicators from dispensers, 4 shows a metallic label with barcode and visually readable number, 5 shows mounting slots, which are slots to secure the subframe to the building structure, 6 shows a metal bracket that provides rigidity, 7 shows a wiring duct which protects the power and communication cables, 8 shows an air connection, 9 shows a power and communications connector, and 10 shows a base plate, which is a dove tail plate to attach the dispenser to the subframe.

In FIG. 25, 1 shows a hopper reserve to hold product to be dispensed, 2 shows the main enclosure, 3 shows a PCB enclosure, which is an enclosure to protect electronics and controls, 4 shows the nozzle used to funnel product into bottles or vials, 5 shows a buffer compartment to hold product before it is dispensed into a bottle or vial, 6 shows a sensor which detects and counts product as it is falling into the buffer, 7 shows a vibrating channel which vibrates and singulates product so that it can be counted, 8 shows a top hatch, which controls access to the product inside the dispenser, 9 shows a vibratory drive which generates vibration that is transmitted to the hopper and channel, 10 shows a locking mechanism that locks the canister and top hatch to prevent access to product, 11 shows a label that is a unique identifier for each dispenser (which generally has a barcode and visible number), 12 shows a canister ID reading pins, which are used to read the canister electronic ID number, and 13 shows a nozzle deflector, which prevents the product from jamming the nozzle.

In FIGS. 27A-27F, the numbers in the figures correspond to the following: 2000-2002 and 2004 show packing stations, order verification stations, label applying stations, and singles packing station, which are adjacent to a forklift aisle, 2003 shows a manual induction station, which is adjacent to a tray full detection device and a automatic scanning device, 2005 shows a single packing line and an autopacker, 2006 shows a capper, 2007 shows a pharmaceutical error checking area, 2008 shows puck conveyor panels, which is adjacent to a maintenance aisle, 2009 shows an A frame and tote conveyor panels, 2010 shows a maintenance platform, 2011 shows ATC replenishment stations, and 2012 shows ATC maintenance stations.

Moreover, the conveyor system can be designed to accommodate a plurality of vials that can wait at a given counting station. In one embodiment, 4 or 5 vials can wait at a counter.

In one embodiment of a prescription filling system, there are a plurality of vial descramblers and a plurality of vial labelers. Empty vials are fed from a descrambler bin into a chute through which the empty vials proceed until a label is applied to the vial by a vial labeler. Labels are applied based on patient-specific prescription orders received and stored in a central computer database. In another embodiment, labels may be applied to vials manually, and the empty, pre-labeled vials placed into the descramblers. In such an embodiment, labeled vials would pass from the descrambler and into a holder or puck as further described below. In another embodiment, labels may be applied manually to vials as the vials are moving from the descrambler through a chute or lane to be placed into a puck or holder. In another embodiment, vials may be pre-labeled off-site or at another location on-site using automated vial labelers, and the pre-labeled, empty vials may be put into the descramblers from which the vials pass to an area where they are placed into and associated with a puck or holder.

After a label is applied to a vial, the vial is placed into a holder or puck that contains an RFID chip for identification purposes. The holders or pucks may be generally cylindrical objects with open tops into which a vial can be placed. Preferably, the holders are shaped such that they are wider and heavier at their base and so that at least a portion of a vial placed within a holder extends out from the top of the holder. A wider and heavier base helps prevent tipping over of the vials as the vials move along the vial conveyor matrix within their holders. In a preferred embodiment, the vial opening is at least about 30 mm in diameter. In one embodiment of a prescription filling system, a single size of vials may be used. In another embodiment, the volume of the vial is determined by the size of the order.

In one embodiment the pucks are diverted by an arrangement of pushers on the conveyer matrix according to the target information for the ATD banks. When parallel processing occurs, a plurality of pucks may pass through to other ATD banks containing a plurality of vials.

The vials may be placed into the holders using manual labor or by an automated system. There may be one or more stations where empty vials are placed into holders. As a vial is placed into a holder, the barcode on the vial label is scanned, and the RFID chip in the holder is read. Both of these identifiers are stored in the central computer and linked together, indicating that a vial for a particular patient order to be filled is traveling through the system in a particular holder. The linking of a labeled vial with a holder allows the central computer to direct where in the vial conveyor matrix the vial proceeds in order to be properly filled. In other words, for example, if a vial is labeled according to a prescription order of 30 tablets of antidepressant for John Doe, the central computer can direct the associated holder, via the RFID chip, to the automated tablet dispensing system within the vial conveyor matrix that contains the ordered antidepressant. Moreover, at or before the time when the tablets are being dumped into the vials/trays, an RFID chip on a puck/holder that is associated with the vial tray is read, which allows dumping only if the correct puck/holder is in position. Further, the present system may have a computer controlled recounting buffer that allows for a continuous counting process.

The control PC, which handles the order queue for the ATD units, may expect pucks to arrive at the correct ATD in the same order as customer orders are received from the PLC/WCS (programmable logic controller/Warehouse control system). When the orders are processed in the order that customer orders are received, one of the following processes occur: 1) the expected puck arrives and the order is processed in the normal manner, 2) the puck does not arrive at the destination lane, which may cause a second order to be sent, 3) an unexpected puck in the correct order queue arrives at the destination lane, which causes that puck to be properly filled, or alternatively, the order will not be filled, 4) the puck arrives that is not in the correct order queue, which causes no product to be dispensed. The system can also be designed so that pucks containing vials/trays can be recycled around conveyor lanes so that they arrive at a destination in a desired order. For example, puck A containing vial A may be filled prior to vial B associated with puck B but puck A can be routed so that it arrives at a given destination after vial B associated with puck B. Exemplary embodiments of automated tablet dispensing systems according to this invention were described in detail above.

The PLC from the PC may optionally stop each puck at a given definition point, wherein a digital camera may be present that takes a photo of the contents of any vial (if product has been dispensed), and the RFID associated with the vial may be used to read the puck-transponder number. The image may be optionally saved at the WCS database and named with the puck transponder number. The saved image may be evaluated by one or more pharmacists or authorized personnel to evaluate the integrity of the vial. The one or more pharmacists may compare the photo of the vial with a standard control or known vial with the correct product to ascertain the integrity of the vial. In one embodiment, if the one or more pharmacists verify the integrity of the vial, the pharmacist(s) press a "yes" button or keystroke which allows the vial then proceeds to the capper. Alternatively, if the pharmacist verifies that the vial does not contain the correct order or some other problem arises, the pharmacist(s) press a "no" button or keystroke, which optionally sends the puck to an error correction station, wherein the error can be corrected and/or reprocessed.

In one embodiment, only those pucks with the associated vials that have received a "yes" from the pharmacist proceed to capping. Thus, pucks that are sent to target check stations by the WCS, pucks that have errors, and pucks that have not been read are sent to the checking station or to the appropriate error correction station(s). In one embodiment, at the appropriate error correction station(s), one or more pharmacists may correctly place product in the vial. Alternatively, the one or more pharmacists may correct the error and place the puck in the system to be repacked by the system. In a preferred embodiment, the puck with the filled vial will again be photographed and checked for its integrity by one or more pharmacists.

As each labeled vial is placed into and associated with a holder, the vial travels to the appropriate location within the vial conveyor matrix for filling according to prescription order. An exemplary vial conveyor matrix includes a plurality of rows of automated tablet dispensing systems extending between entrance and exit lines running along the outside of each end of these rows. Conveyor lines extend from the outside entrance and exit lines along each side of each row of automated tablet dispending systems. These conveyor lines are connected by shorter conveyor lines that extend underneath each automated tablet dispensing system.

In an exemplary embodiment, a vial conveyor matrix includes a plurality of rows (e.g., 5, 10, 12, 15, 20, 25, or any other number) with each row having a plurality of automated tablet dispensing systems (e.g., 5, 10, 12, 15, 20, 25, or any other number), such that the vial conveyor matrix includes two outside entrance lines, two outside exit lines, numerous lines extending between the outside lines, and numerous lines extending underneath the automated tablet dispensing systems. The number of rows and automated tablet dispensing systems on each row may be determined by the desired throughput of the prescription filling system, the different number of drug types that are to be dispensed by the system, or other parameters. Multiple automated tablet dispensing systems may dispense the same type of drug. For example, it may be desirable to have several automated tablet dispensing systems dedicated to dispensing frequently ordered drugs. Each row is not required to have the same number of automated tablet dispensing systems. An exemplary embodiment, a prescription filling system may include 15 rows including a cumulative total of 460 automated tablet dispensing systems. It should be understood that any number of automated tablet dispensing systems may be used in a variety of configurations (not limited to rows) in accordance with the principles of this invention.

As an example of a process for filling a vial, as a labeled vial in its holder proceeds toward the appropriate automated tablet dispensing system, the vial travels along one of the outside entrance lanes. When the vial reaches the row where the appropriate automated tablet dispensing system is located, the vial exits onto the entrance conveyor line for that row of dispensing systems. The vial travels that conveyor line, until it reaches the appropriate automated tablet dispensing system, where the vial then proceeds onto the shorter line that travels underneath the dispensing system. The vial continues to move forward along the line, waiting on vials ahead of it in line for that dispensing system to be filled, until the vial is underneath the nozzle of the dispensing system. Once the empty vial is under the nozzle, the automated dispensing system empties pre-counted tablets into the vial according to the patient-specific prescription order. The location of the holder is known by the central computer at all times using the RFID chip. The central computer communicates with the control board of each automated tablet dispensing system such that the automated tablet dispensing system can pre-count tablets for vials before the vial reaches the point where it is to be filled. This allows for increased filling of prescription orders because the automated tablet dispensing system does not have to wait until an empty vial is beneath the nozzle to both count and then empty tablets into the vial. Moreover, it is noted that a plurality of vials can be filled simultaneously. In an exemplary embodiment, any number of vials can be filled simultaneously.

After filling, a filled vial exits the conveyor line that passes underneath the automated tablet dispenser and proceeds along a conveyor line toward the outside exit lines. The filled vial enters an outside exit line and may proceed to a verification station before capping. The vial and holder may pass through a station where the vial label barcode and holder RFID chip are read to verify that the vial and holder still match (i.e., there has not been any tampering, the vial has not switched with another vial with the wrong drug, etc.). A manual check by a pharmacist may also be performed prior to capping to confirm the order is properly filled. In one embodiment, a pharmacist performs a visual inspection of the contents of the vial and compares the visual contents to an image of what the drug in the vial is supposed to be. The image available to the pharmacist is from a computer database and is provided on a computer screen at the pharmacist's station as the holder passes over a station that identifies the holder (and thus the associated vial and drug). If there are no problems with the filled vial, the pharmacist then hits an appropriate key or keys on his computer terminal and the holder and vial are allowed to proceed to capping. If there are any problems, the pharmacist may manually remove the holder and vial from the line, or, alternatively, the pharmacist may be required to hit a key or keys on his computer terminal indicating the problem with the filled vial and the filled vial may proceed on another line to a mistake area where errors are collected. In another embodiment, rather than making a visual inspection of the contents of the filled vial, the pharmacist compares an image of the contents of the filled vial previously taken during processing with an image from a computer database of what the drug in the vial is supposed to be.

After being filled, and optionally verified and checked by a human operator, each filled vial is ready to be capped. In a preferred embodiment, the pucks containing vials are sent to the capper. The capper may optionally contain an alternating cap chuck and indexing stepper drive that allows the introduction of pucks containing vials to the cap head. After capping, any capped vials proceed to an accumulation line to feed the vials into totes. After filling, the vials are removed from the holders/pucks and the holders/pucks are circulated by a conveyor line or lines back to the labeling area of the prescription filling system for reuse.

The filled vials of a patient's prescription order may be packed manually or by an automatic packing machine. Alternatively, a patient's prescription order may be combined with additional pre-packaged goods/items by an automatic picking machine (such as the A-frame machine available from Knapp Logistics & Automation that is well known to those skilled in the art) or manual picking before proceeding to packing. Other machines are contemplated such as an LMS machine or and MDS machine, which are well known to those of skill in the art. Packaging of a patient's order for shipment may be done manually or by an automated packing system based on any number of parameters set by the administrator of the prescription filling system.

In an exemplary embodiment according to this invention, an automated packing system provides integrated processing of orders for packaging. As a tote or multiple totes enter the automatic packing machine from a conveyor line, the packer reads the RFID chip in the tote that identifies the order or a part of an order. The tote or multiple totes identity is/are verified and the packer prints an order document that details the prescriptions and other goods/items, if any, ordered for inclusion in the packed shipment. For example, if one location has a multitude of orders that must be sent to that location, one can program the PLC and/or the WCS to pack those orders together. The order document is scanned after printing and the RFID chips of the tote or multiple totes is/are read again to confirm a match. A shipping label is printed and similarly verified to match the tote and order document. The order is then packed for shipment as the tote contents are emptied into a packing area, and the shipping label is applied to the package. Packages may then move to a pre-sorting area where they are pre-sorted for shipment, if desired.

The present invention also provides systems and methods for automated packaging with increased efficiency and reduced errors. Certain embodiments of systems and methods of the invention may provide one or more of the following functionalities: packaging of orders from multiple conveyor systems; handling of numerous order types, including pre-packaged goods/items and vials filled to customer order; insertion of custom literature into final package; volumetric sensing that enables dynamic sizing of the final package; creation of custom internal bag/carton labels for final package; creation and application of custom external shipping labels onto final package; bar code and RF identification to validate final package contents; error correction station; and a final package sorter to enhance shipping efficiency.

A customer's order is typically entered into a central computer system that controls order flow and processing. A typical subsystem of totes and conveyors collects all prepackaged goods/items from an automated storage warehouse. Individual customer orders are collected in a single tote. In a preferred embodiment, another subsystem places labels on each vial before filling the vials, dispenses medication in the vials and then caps the vials. The goods/items in the totes and vials are then transported to an automated packaging system by a system of conveyors where the contents of the totes are combined with the vials and packaged for shipping as further described below.

Figure 26:
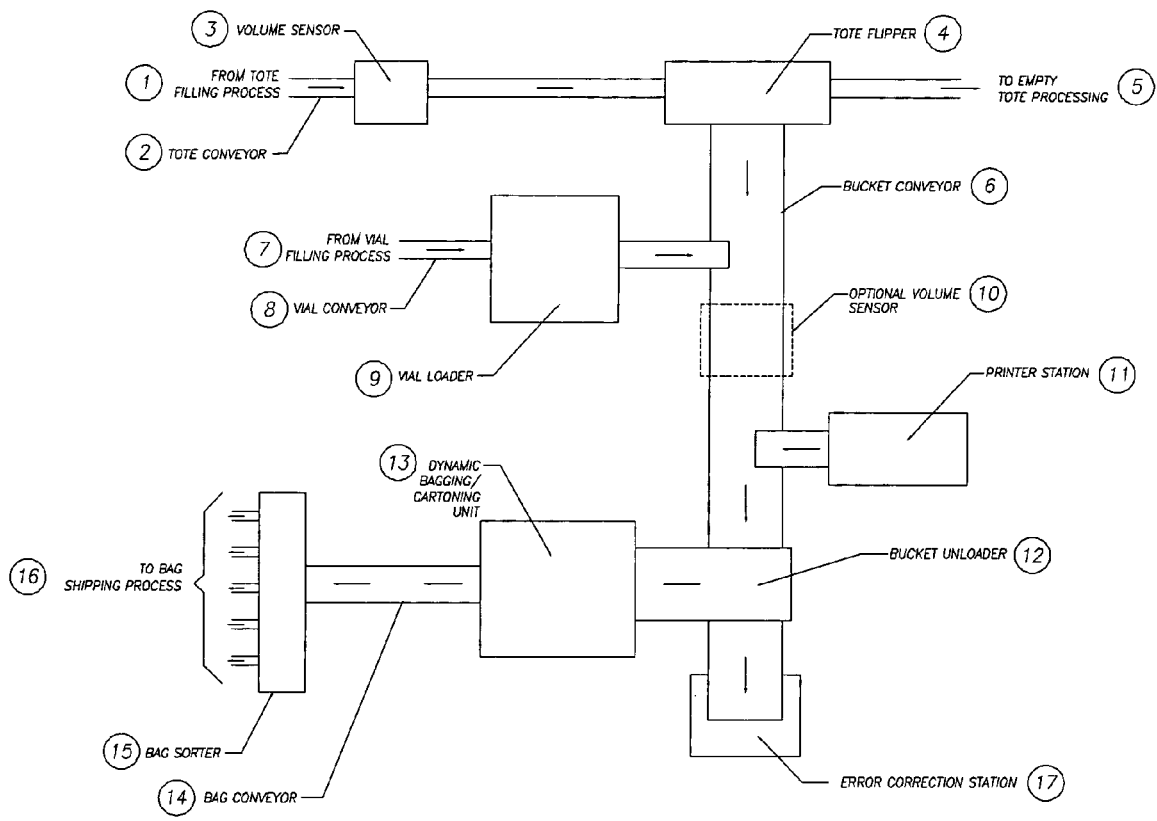
FIG. 26 shows a block diagram of an embodiment of an automated packing system for prescriptions and other goods/items according to this invention.
Figure 27A:
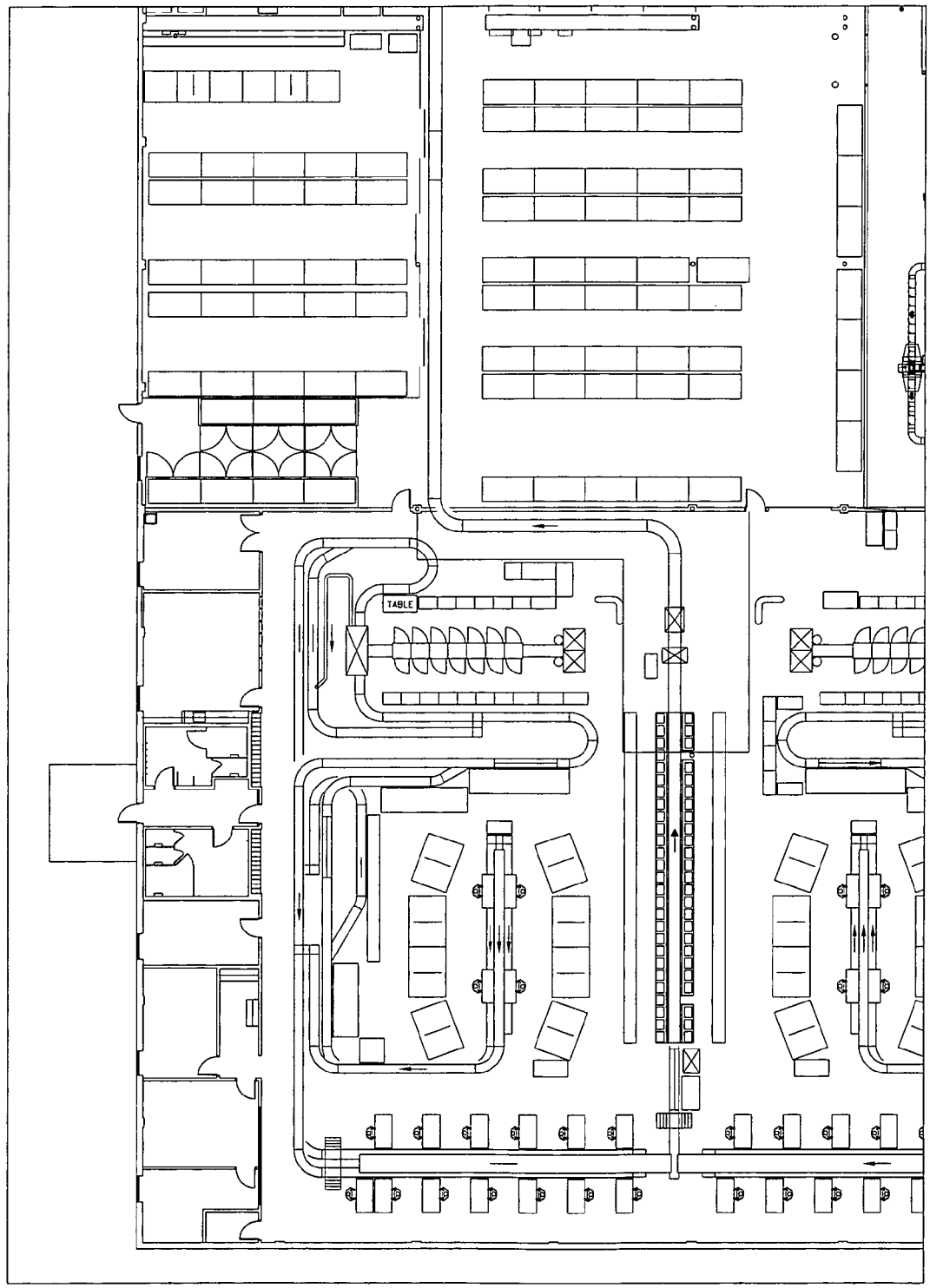
FIGS. 27A-27F show another exemplary embodiment of a prescription filling and patient order packaging system according to this invention.
Figure 27B:
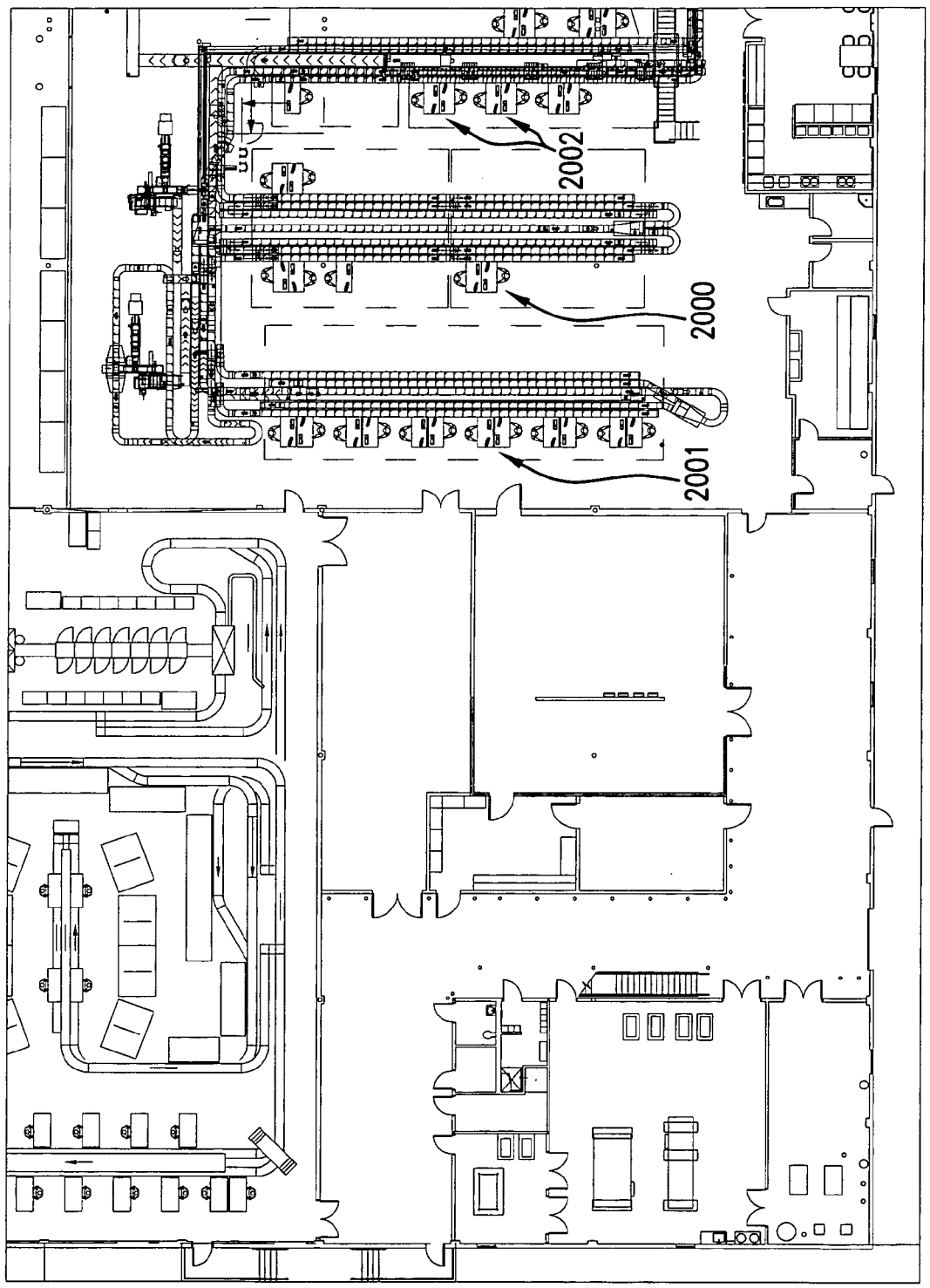
Figure 27C:
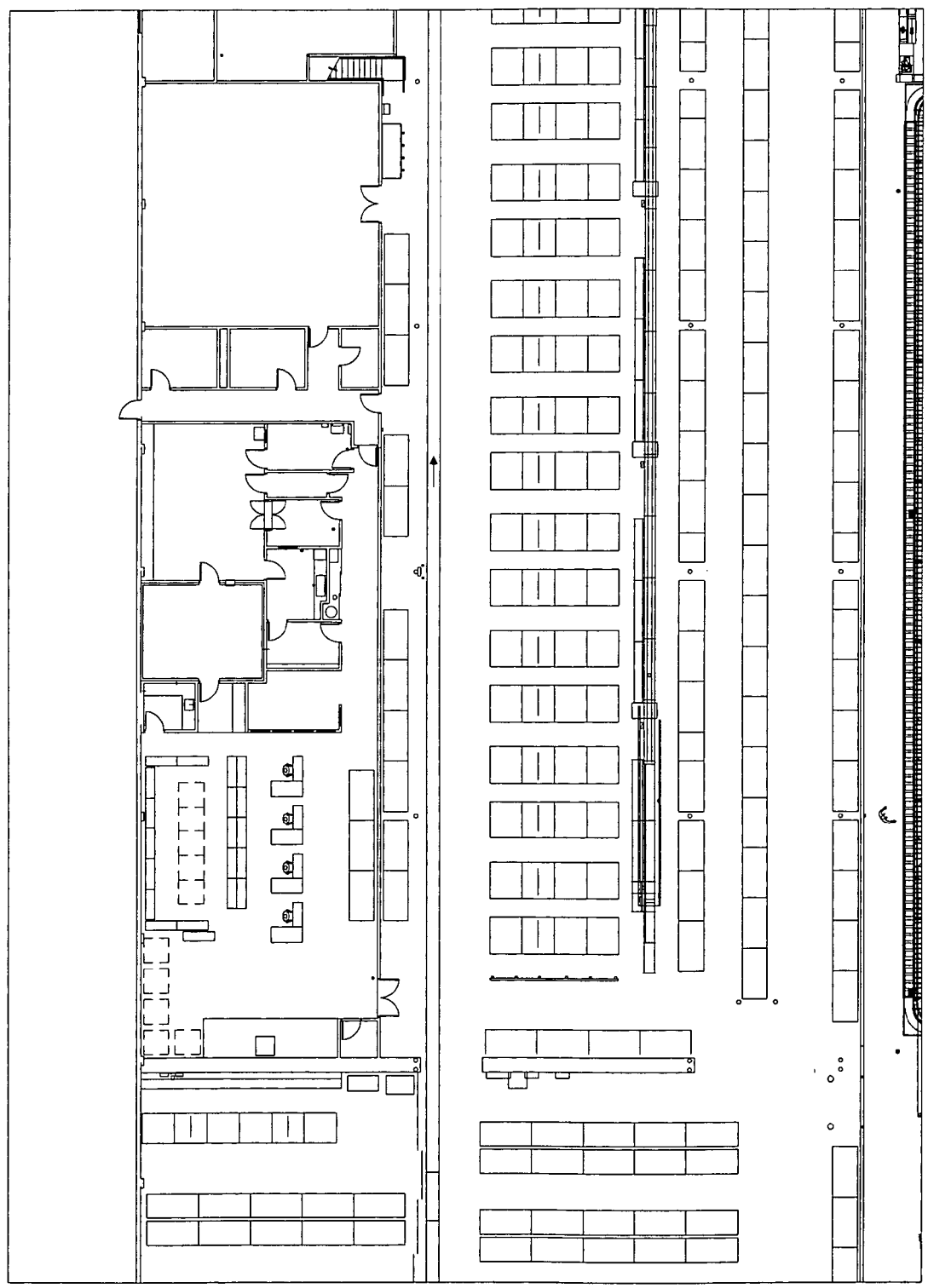
Figure 27D:
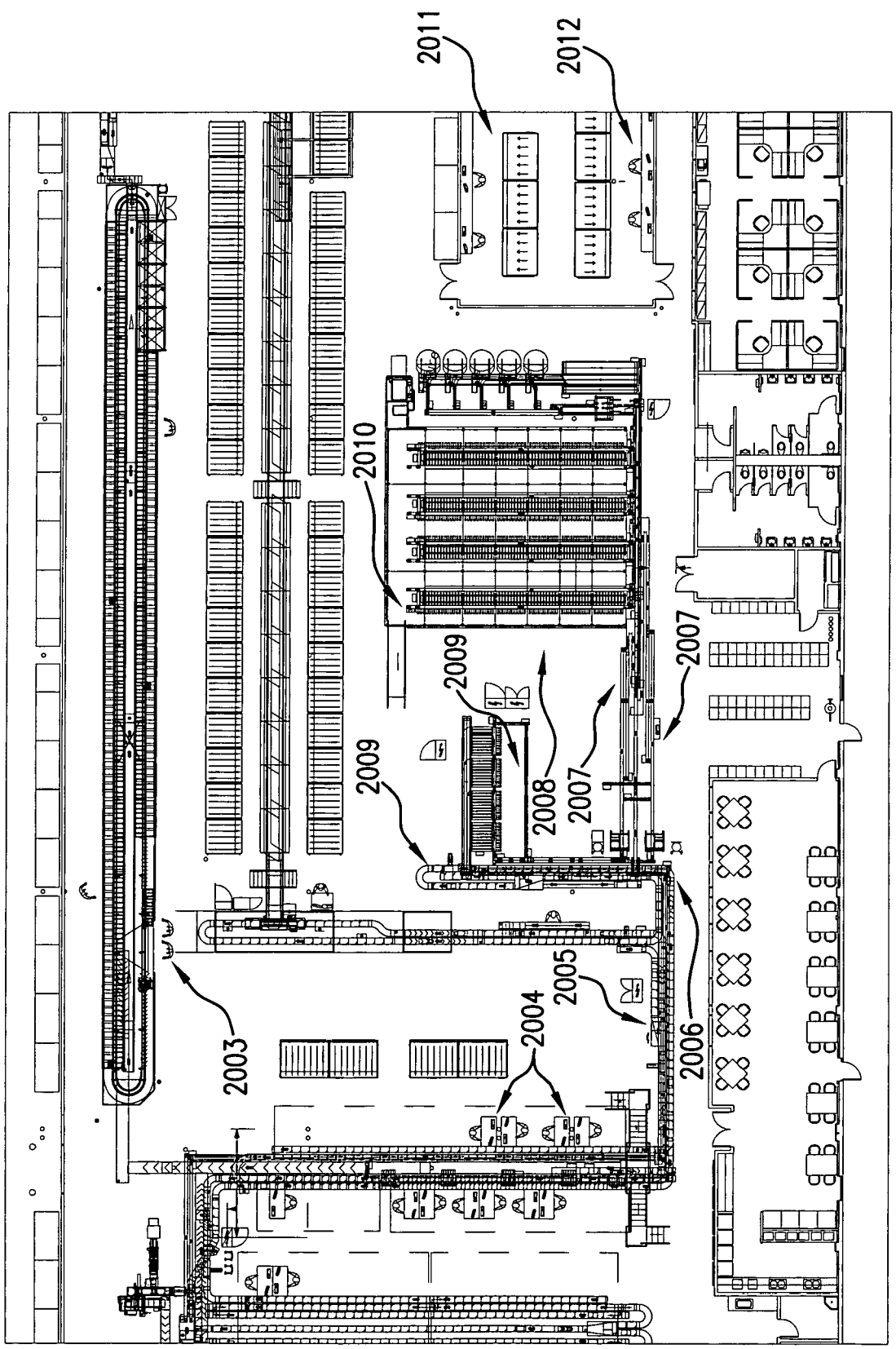
Figure 27E:
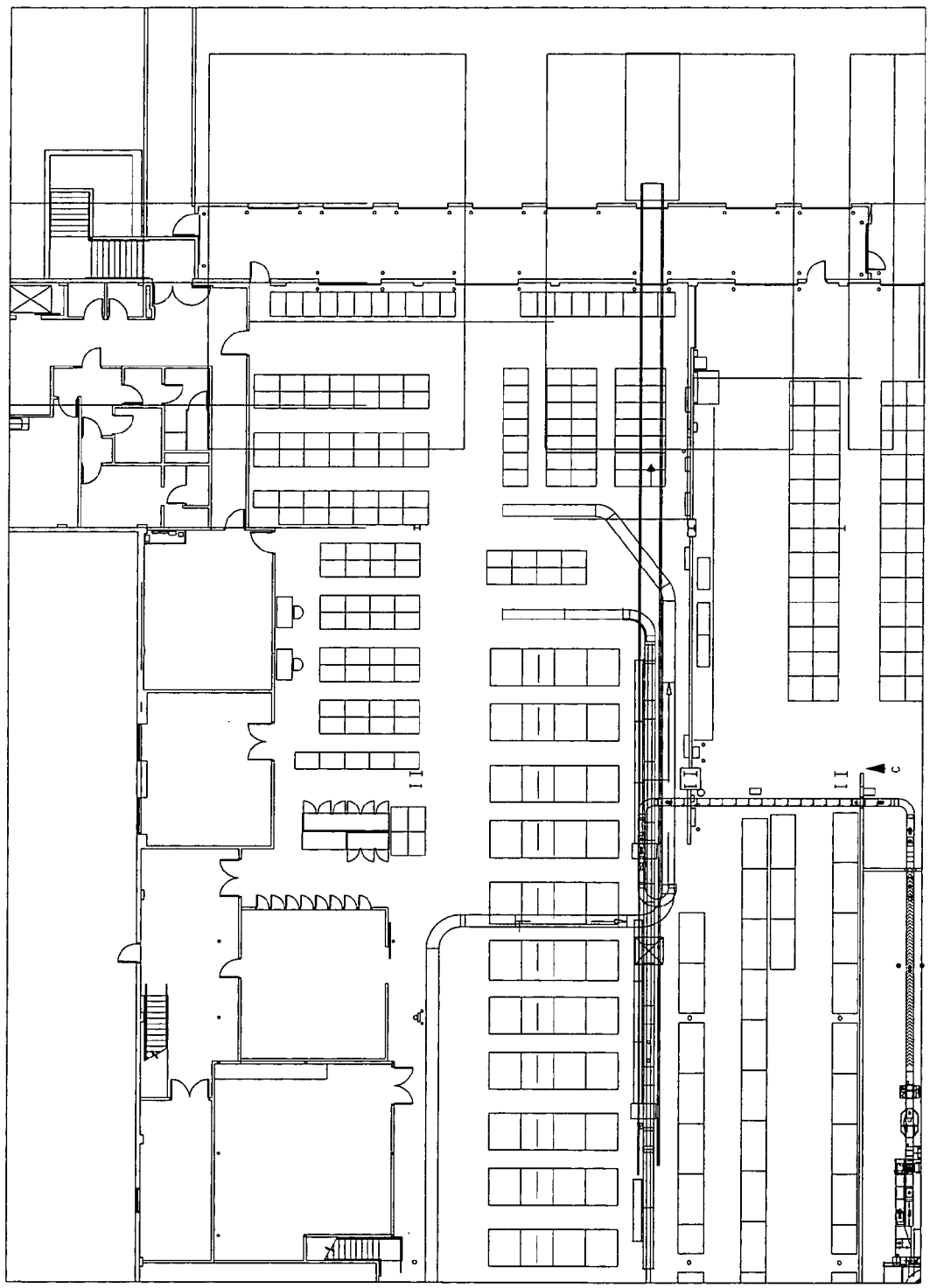
Figure 27F:
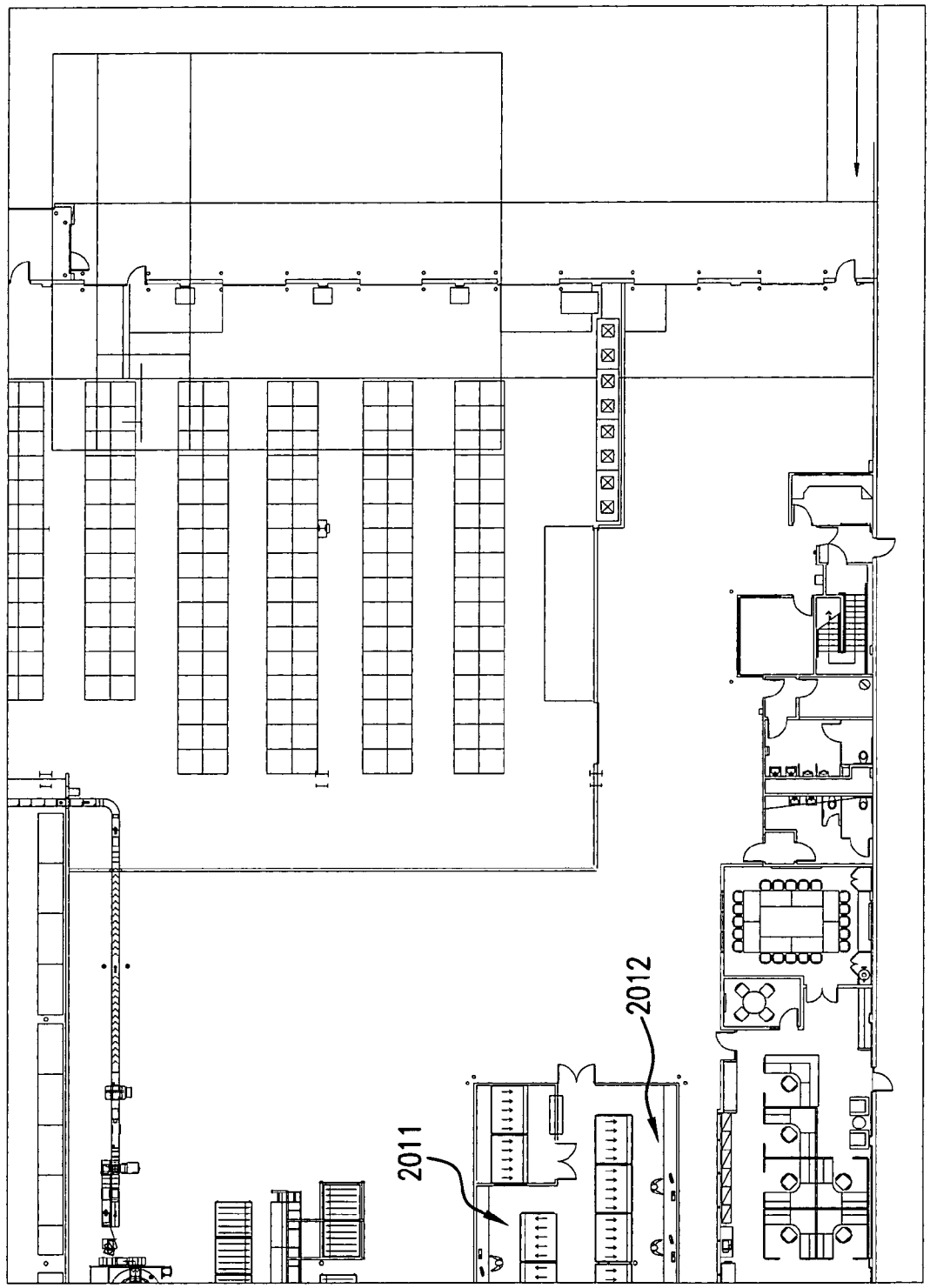

Referring now to FIG. 26, each individual customer order of prepackaged goods/items is placed, either manually or by a tote filling subsystem 1, into a radio frequency (RF) identified tote bin. A tote conveyor 2 transports the tote from the filling process to a volume sensor 3 that determines the final package volume required.

Tote conveyor 2 then transports the tote bin to a tote flipper 4. Tote flipper 4 is preferably Knapp Model BHEL, available from Knapp Logistics & Automation of Cartersville, Ga., U.S.A., but other commercially available tote flippers well known to those skilled in the art are suitable as well. Tote flipper 4 empties the contents of the tote bin into a divided section of a bucket conveyor 6, and returns the empty tote bin 5 to be reused in the tote filling subsystem. Each divided section of bucket conveyor 6 is RF identified and represents an individual customer order or a portion of an order. An embodiment of an automated packaging system may include multiple tote filling subsystems, tote conveyor lines, volume sensors, and tote flippers for each bucket conveyor 6.

Pre-filled vials of medication are transported by a vial conveyor 8 to a vial loader 9 from a manual or automated vial filling subsystem 7. Vial loader 9 places the appropriate vial into the appropriate divided section of bucket conveyor 6 that corresponds to an individual customer order or a portion of an order. Modifications are considered to be within the scope of the invention such as modifying the system to package orders containing goods/items and/or vials from several different customers together that are subsequently sent to the same location. An optional volume sensor 10 determines the final order package volume required, including any vials from vial loader 9. Volume sensor 10 operates in substantially the same manner as volume sensor 3 described above. The volume of the vials after filling is often a known value and, in certain embodiments of systems and methods of this invention, may simply be added to the volume value obtained by volume sensor 3 to calculate a final order package volume. An embodiment of an automated packaging system may include multiple vial filling subsystems, vial conveyor lines, and vial loaders for each bucket conveyor 6.

A printer station 11 prints and folds custom literature (e.g., instructions, packing lists, advertisements, etc.), sometimes referred to as lit-packs, and internal bag/carton labels and places them into the appropriate divided section of the bucket conveyor 6 that corresponds to an individual customer order. An embodiment of an automated packaging system may include multiple printer stations. Printer station 11 is preferably a P.S.I. "Autoslip" Model, available from PSI Peripheral Solutions Inc., Amherst, N.Y., U.S.A. or Mississauga, Ontario, Canada.

A bucket unloader 12 completely empties one or more of the divided sections of bucket conveyor 6 into a dynamic bagging/cartoning unit 13. It is contemplated that not only may one have either a dynamic bagging unit or a dynamic cartoning unit but in a preferred embodiment, the system may contain both a dynamic bagging unit and a dynamic cartoning unit. Having both a dynamic bagging unit and a dynamic cartoning unit allows an order to be either bagged or cartoned or allows a mix of the two. In a preferred embodiment the cartoning is made of corrugated cardboard. Bucket unloader 12 empties the divided sections of bucket conveyor 6 only after matching the RF identification of the sections to the bar code on the internal bag/carton label. If a mismatch occurs, the contents of the divided section are transported by bucket conveyor 6 to an error correction station 17 for manual processing.

Upon receiving the contents from the bucket unloader, dynamic bagging/cartoning unit 13 sizes the bag/carton required according to the volume of the order, as detected by volume sensors 3 and/or 10 or a calculation such as that described above, seals the bag/carton, and places an external shipping label on the final package. Dynamic bagging/cartoning unit 13 can be obtained from Belk of Germany, but other bagging/cartoning units well known to those skilled in the art may be used. The final package is transported by a bag/carton conveyor 14 to a bag/carton sorter 15 that pre-sorts the completed orders for shipping 16 to the customer. An embodiment of an automated packaging system may include multiple bucket unloaders, dynamic bagging/cartoning units, bag/carton conveyor lines, and bag/carton sorters for each bucket conveyor 6.

The system for automatic packaging of goods/items, as described previously has the following advantages:

a) an ability to size a bag or a carton according to the volume of goods/items, b) an ability to consolidate the goods/items into either of bags or cartons or a mix of bags and cartons, c) an ability to add bags or cartons to an order, d) an ability to hold, sequence and sort orders.

To Applicants knowledge, all of these traits are heretofore unknown.

An additional advantage that the automated packaging system of the invention has over other packaging systems is that the instant automated packaging system allows either distribution order oriented packaging or end of the line packaging or both. This is in contrast to presently available packaging systems that use only end of the line packaging systems. Moreover, the automated packaging system of the instant invention allows for multi-line and single line order packaging, including an ability to combine different packaging materials, such as bags and cartons.

The foregoing description of the exemplary embodiments of the invention has been presented only for the purposes of illustration and description and is not intended to be exhaustive or to limit the invention to the precise forms disclosed. Many modifications and variations are possible in light of the above teaching. The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Moreover, it is contemplated and within the scope of the instant invention to combine any embodiment of the above-described invention with any other embodiment.

What is claimed is:

1. A system for automated tablet dispensing comprising: a canister that holds tablets and is removably engaged with a counter; the counter including: a hopper assembly that receives tablets from the canister and transfers the tablets to a sensor, the hopper assembly including a dispenser reserve, singulation channels, and a vibrator; the sensor, which counts the tablets; and a buffer with two compartments that hold counted tablets before releasing the counted tablets into vials; and a nozzle assembly through which counted tablets from the buffer are emptied into individual vials or trays.

2. The system according to claim 1, wherein the canister further comprises an access door.

3. The system according to claim 2, wherein the canister has openings on either side that allow the insertion of a tamper proof security tag.

4. The system according to claim 1, wherein the canister contains a unique serial number that dedicates said canister to the sensor.

5. The system according to claim 1, wherein the sensor contains a scanner.

6. The system according to claim 5, wherein the scanner is selected from the group consisting of an electrostatic field scanner, an IR sensor, and a light barrier type sensor.

7. The system of claim 1, further comprising a capper.

8. The system of claim 7, wherein the capper comprises at least one alternating cap chuck and/or indexing stepper drive.

9. The system of claim 1, further comprising at least one vial descrambler and/or vial labeler.

10. The system of claim 9, wherein the system contains at least one of both the vial descrambler and vial labeler.

11. The system of claim 1, wherein the system is in a secure room.

12. The system of claim 11, wherein the system further comprises a pharmacist.

13. The system of claim 12, further comprising a replenishment technician.

14. The system of claim 1, wherein said buffer with two compartments has at least one flipper door.

15. The system of claim 14, wherein each of the two compartments has a capacity of about 180 cubic centimeters.

16. The system of claim 1, further comprising electronics for the system wherein the electronics comprise a control board and one or more pneumatic valves.

17. The system of claim 1, wherein the buffer contains additional compartments.

18. The system of claim 1, wherein the vibrator assists in moving the tablets down the singulation channels.

19. The system of claim 1, further comprising a computer-based system capable of calibrating the system to accommodate a plurality of tablet sizes.

20. A system for automated tablet dispensing comprising: a canister that holds tablets and is removably engaged with a counter; the counter including: a hopper assembly that receives tablets from the canister and transfers the tablets to a sensor, the hopper assembly including a dispenser reserve, singulation channels, and a vibrator; the sensor, which counts the tablets; and a buffer with two compartments that hold counted tablets before releasing the counted tablets into vials; and a nozzle assembly through which counted tablets from the buffer are emptied into individual vials or trays, wherein the dispenser reserve and vibrator are balanced so that the tablets flow at a constant rate.

* * * * *